(12) United States Patent
Fishbein

(10) Patent No.: US 8,427,160 B2
(45) Date of Patent: Apr. 23, 2013

(54) SUSCEPTIBILITY-MATCHED MULTI-WELL SAMPLE HOLDERS FOR HIGH-THROUGHPUT SCREENING BY MAGNETIC ANALYSIS

(75) Inventor: Kenneth W. Fishbein, Laurel, MD (US)

(73) Assignee: The Government of the United States of America, as represented by the Secretary, Department of Health and Human Services, Washington, DC (US)

( * ) Notice: Subject to any disclaimer, the term of this patent is extended or adjusted under 35 U.S.C. 154(b) by 760 days.

(21) Appl. No.: 12/083,501

(22) PCT Filed: Oct. 12, 2006

(86) PCT No.: PCT/US2006/039048
§ 371 (c)(1),
(2), (4) Date: Dec. 30, 2008

(87) PCT Pub. No.: WO2007/047149
PCT Pub. Date: Apr. 26, 2007

(65) Prior Publication Data
US 2009/0160439 A1  Jun. 25, 2009

Related U.S. Application Data

(60) Provisional application No. 60/725,299, filed on Oct. 12, 2005.

(51) Int. Cl.
*G01V 3/00* (2006.01)
(52) U.S. Cl.
USPC ........................................... 324/319; 324/320

(58) Field of Classification Search .................. 324/321, 324/320, 318
See application file for complete search history.

(56) References Cited

U.S. PATENT DOCUMENTS

| 4,549,136 | A |   | 10/1985 | Zens |
| 4,654,592 | A |   | 3/1987 | Zens |
| 5,302,900 | A | * | 4/1994 | Cummings ................... 324/321 |
| 5,545,994 | A |   | 8/1996 | Barbara |

(Continued)

FOREIGN PATENT DOCUMENTS

| EP | 1 331 488 | 7/2003 |
| WO | WO-01/33257 | 5/2001 |

OTHER PUBLICATIONS

Zhang et al., Establishment and implications of a characterization method for magnetic nanoparticle using cell tracking velocimetry and magnetic susceptiblity modified solutions, Analyst, 2005, 130, 514-527.

(Continued)

*Primary Examiner* — Louis Arana
(74) *Attorney, Agent, or Firm* — Polsinelli Shughart PC; Teddy C. Scott, Jr.; Ari Bai

(57) ABSTRACT

A method of performing high throughput magnetic sensing of one or more samples. The method comprises selecting a first sample having a first bulk magnetic susceptibility, selecting an assay plate having a second bulk magnetic susceptibility matched to the first bulk magnetic susceptibility, the assay plate including multiple wells, introducing the first sample into a plurality of the wells, and performing magnetic sensing on the plurality of wells containing the first sample. Assay plates, caps, kits, and other devices and methods relating to high throughput magnetic sensing are also disclosed.

27 Claims, 20 Drawing Sheets

U.S. PATENT DOCUMENTS

| | | | |
|---|---|---|---|
| 5,573,567 | A | 11/1996 | Shigezane |
| 5,831,434 | A | 11/1998 | Shigezane et al. |
| 6,307,372 | B1 | 10/2001 | Sugarman et al. |
| 6,504,368 | B2 | 1/2003 | Ross et al. |
| 7,075,303 | B2 * | 7/2006 | Cavaluzzi et al. ............ 324/321 |
| 7,612,563 | B2 * | 11/2009 | Massin et al. ................. 324/321 |
| 7,656,158 | B2 * | 2/2010 | Fey et al. ...................... 324/321 |
| 2003/0049867 | A1 | 3/2003 | Selifonov et al. |
| 2004/0164738 | A1 | 8/2004 | Raftery et al. |
| 2005/0024055 | A1 | 2/2005 | Cavaluzzi et al. |

OTHER PUBLICATIONS

Keyser et al., Magnetic susceptibility of some materials used for apparatus construction (at 295 K), Rev. Sci. Instrum., vol. 60, No. 8, Aug. 1989, 2711-2714.

Stockman, Flow NMR spectroscopy in drug discovery, Current Opinion in Drug Discovery & Development, 2000, vol. 3, No. 3, 269-274.

Holmes et al., Accelerated toxicity screening using NMR and pattern recognition-based methods, Current Opinion in Drug Discovery & Development, 2000, vol. 3, No. 1, 72-78.

Hicks, Recent Advances in NMR: Expanding its Role in Rational Drug Design, Current Medicinal Chemistry 2001, 8, 627-650.

Haner et al., Small Volume Flow Probe for Automated Direct-Injection NMR Analysis: Design and Performance, Journal of Magnetic Resonance 143, 69-78, 2000.

Evans et al., Evaluation of a Range of MRI-Active pH Indicators Using a Multiple-Sample Method, AIChE Journal, May 2005, vol. 51, No. 5, 1541-1547.

MacNamara et al., Multiplex sample NMR: an approach to high throughput NMR using a parallel coil probe, Analytica Chimica Acta 397, (1999), 9-16.

Ballon et al., Resolution Enhanced NMR Spectroscopy in Biological Systems via Magnetic Susceptibility Matched Sample Immersion Chambers, Communications, 754-758, (1983).

Metz et al., Reference Deconvolution: A Simple and Effective Method for Resolution Enhancement in Nuclear Magnetic Resonance Spectroscopy, 21-42.

Högemann et al., "High Throughput Magnetic Resonance Imaging for Evaluating Targeted Nanoparticle Probes", Bioconjugate Chem., 2002, pp. 116-121, vol. 13, No. 1.

Conolly et al., "Positive Contrast MRI of Cells Labeled with Magnetic Nanoparticles".

Ross et al., "Application of Chemical Shift Imaging for Simultaneous and Fast Acquisition of NMR Spectra on Multiple Samples", Angew. Chem. Int. Ed. 2001, pp. 3243-3245, vol. 40, No. 17.

Kotyk et al., "High-Throughput Determination of Oil Content in Corn Kernels Using Nuclear Magnetic Resonance Imaging", JAOCS, 2005, pp. 855-862, vol. 82, No. 12.

Chemla et al., "Ultrasensitive magnetic biosensor for homogeneous immunoassay", Proceedings of the National Academy of Sciences of the USA, Dec. 19, 2000, pp. 14268-14272, vol. 97, No. 26.

Evans et al., "Efficient Magnetic Resonance Imaging Methods for Automated Quantitation of Magnetic Resonance Parameters from Multiple Samples", Magnetic Resonance in Chemistry, 1997, pp. S76-S80, vol. 35.

Doty et al., "Magnetism in High-Resolution NMR Probe Design. I: General Methods", Concepts in Magnetic Resonance, 1998, pp. 133-156, vol. 10, No. 3.

* cited by examiner

SUSCEPTIBILITY-MATCHED MULTI-WELL SAMPLE HOLDERS FOR HIGH-THROUGHPUT SCREENING BY MAGNETIC ANALYSIS

BACKGROUND

The present invention relates generally to the field of magnetic sensing, such as magnetic resonance imaging (MRI) and nuclear magnetic resonance (NMR) spectroscopy. More particularly, the present invention relates to multi-well sample holders, such as assay plates, that are used in these processes. The multi-well sample holders are formed of a material having a magnetic susceptibility that is matched to the samples being analyzed. The present invention further relates to methods of performing high-throughput screening using magnetic sensing techniques.

Multi-well assay plates are used in a wide variety of high-throughput measurements in clinical chemistry and immunology, as well as in drug discovery and other research applications. Magnetic resonance imaging (MRI) of multi-well plates offers the possibility of performing new kinds of high-throughput assays, including the detection of targeted magnetic nanoparticles attached to analytes (e.g., located on or within cells). Moreover, MRI-guided localized nuclear magnetic resonance (NMR) spectroscopy could be used to perform high-throughput analyses of complex mixtures of chemicals not possible by any other common analytical technique. Best of all, conventional MRI techniques exist which could permit all samples in one or more multi-well plates to be analyzed simultaneously. However, conventional multi-well assay plates typically exhibit poor performance for MRI-based assays, since they provide inadequate matching of the magnetic susceptibility between the sample (e.g., the solvent and solute) and it surroundings. This results in complex distortion of the magnetic field around each sample, as well as between samples. This has undesirable effects, such as deteriorating the detection limit for magnetic nanoparticles, or rendering it impossible to resolve NMR spectra for individual samples. As a result of these and other drawbacks associated with conventional multi-well assay plates, high-throughput analysis using some types of magnetic analysis (e.g., chemical analysis using localized NMR) has been impractical or impossible. For example, it has been difficult or impossible to obtain NMR spectra directly from individual wells of a multi-well plate (i.e., without transferring the contents of each well to one or more NMR tubes or flow cells).

What is needed, therefore, is a multi-well sample holder and related methods that overcome the shortcomings of the prior art offerings, such as, the reduction in sensitivity, resolution, and signal-to-noise ratio caused by the inhomogeneities of the magnetic field that result from susceptibility variations when using conventional sample holders.

SUMMARY

The present invention relates to multi-well sample holders, such as assay plates, that are magnetic susceptibility-matched to the samples being analyzed therein. Further enhancement in susceptibility matching can be accomplished by combining the sample holders with magnetic susceptibility-matched plugs for each well, e.g., plugs constructed from the same material as the plates. The plugs can eliminate the air-sample interface and associated field inhomogeneities. The plugs can be integrated into a single "cap mat." The entire assembly can be filled and manipulated by standard robotic laboratory equipment already in wide use, e.g., in the pharmaceutical industry, in clinical laboratories, in quality control laboratories, and in combinatorial chemistry. The susceptibility matched design reduces magnetic field distortions around each sample, as well as in between samples. As a result, the present invention dramatically improves spectral resolution and sensitivity in high-throughput NMR analysis, and improves the detection limit for high-throughput MRI imaging of magnetic particles, such as targeted magnetic nanoparticles.

According to one exemplary embodiment, the present invention provides a method of performing high throughput magnetic sensing of one or more samples, the method comprising: selecting a first sample having a first bulk magnetic susceptibility; selecting an assay plate having a second bulk magnetic susceptibility matched to the first bulk magnetic susceptibility, the assay plate including multiple wells; introducing the first sample into a plurality of the wells; and performing magnetic sensing on the plurality of wells containing the first sample.

According to another exemplary embodiment, the present invention provides a method of making an assay plate. The method can comprise: determining the first bulk magnetic susceptibility of a sample to be analyzed in the assay plate; selecting a material having a second bulk magnetic susceptibility matching the first bulk magnetic susceptibility; and forming a multi-well assay plate from the material.

According to another exemplary embodiment, the present invention provides a kit for use in performing high throughput magnetic sensing of a plurality of samples. The kit can comprise: an inventory of solvents having different first bulk magnetic susceptibilities; and an inventory of assay plates having different second bulk magnetic susceptibilities; wherein at least some of the first bulk magnetic susceptibilities are matched to the second bulk magnetic susceptibilities.

According to another exemplary embodiment, the present invention provides n assay plate for analyzing at least a first sample having a first bulk magnetic susceptibility, the assay plate comprising: a plate constructed from a material having a second bulk magnetic susceptibility matched to the first bulk magnetic susceptibility; and a plurality of wells located in the plate for holding the first sample; wherein the plate is adapted for high throughput magnetic sensing of at least the first sample.

According to another exemplary embodiment, the present invention provides a cap for plugging a well of a multi-well assay plate. The cap can comprise: a cap body adapted to plug a well for holding a sample having a first bulk magnetic susceptibility, the cap body constructed of a material having a second bulk magnetic susceptibility matched to the first bulk magnetic susceptibility; and at least one vent hole located in the cap body, wherein the vent hole permits evacuation of air located in the well between the cap body and the sample.

According to another exemplary embodiment, the present invention provides a mat for plugging a plurality of wells of a multi-well assay plate, the mat comprising: a plurality of interconnected cap bodies adapted to plug at least some of the wells of the multi-well assay plate, each of the wells adapted to hold a sample, at least one of which has a first bulk magnetic susceptibility; wherein the interconnected cap bodies are constructed from a material having a second bulk magnetic susceptibility that is matched to the first bulk magnetic susceptibility.

Further objectives and advantages, as well as the structure and function of preferred embodiments will become apparent from a consideration of the description, drawings, and examples.

BRIEF DESCRIPTION OF THE DRAWINGS

The foregoing and other features and advantages of the invention will be apparent from the following, more particular description of a preferred embodiment of the invention, as illustrated in the accompanying drawings, wherein like reference numbers generally indicate identical, functionally similar, and/or structurally similar elements.

DETAILED DESCRIPTION

Embodiments of the invention are discussed in detail below. In describing embodiments, specific terminology is employed for the sake of clarity. However, the invention is not intended to be limited to the specific terminology so selected. While specific exemplary embodiments are discussed, it should be understood that this is done for illustration purposes only. A person skilled in the relevant art will recognize that other components and configurations can be used without departing from the spirit and scope of the invention. All references cited herein are incorporated by reference as if each had been individually incorporated.

Figure 1:
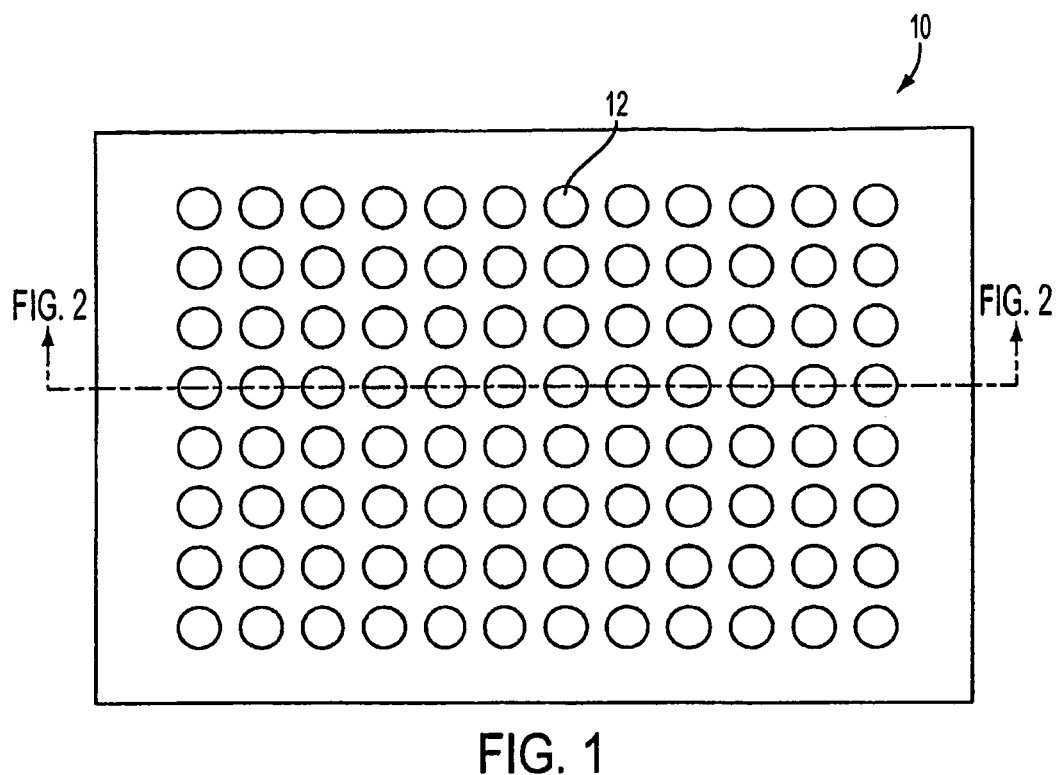
FIG. 1 is a top view of an assay plate according to a first exemplary embodiment of the present invention.

Referring to FIG. 1, an exemplary embodiment of a multi-well sample holder according to the present invention is shown as an assay plate. Assay plate 10 generally comprises a plate of material having an array of wells 12 defined therein. Each of the wells 12 can hold a sample, such as a chemical mixture, to be analyzed using magnetic detection such as, for example, MRI imaging, NMR spectroscopy, localized NMR spectroscopy, magnetic force microscopy, and SQUID-detection. The assay plate 10 can also be used to analyze the samples using non-magnetic techniques, such as optical scanning. The exemplary embodiment of assay plate 10 shown in FIG. 1 includes 96 cylindrical wells arranged in an 8×12 array, however, other quantities and arrangements of wells are possible. For example, assay plate 10 may alternatively have 6, 12, 16, 24, 98, 384, 1024, or 1536 wells. Further, the wells may have hexagonal, square, rectangular, spherical, or other shapes.

The assay plates according to the present invention may advantageously have the same shape and dimensions as conventional multi-well plates, a format that is very widely used in many fields. This has the advantage of allowing the inventive well plates to be used for high-throughput analyses using numerous existing techniques and/or instrumentation, even in addition to magnetic sensing, for example, optical scanning. This also facilitates use of the inventive well plates with widely-used analytical instruments, and/or robotic handling equipment. In many instances, this can eliminate the need to remove the samples from the assay plates, reducing the risk of sample contamination and/or sample loss. Further, using the plates of the present invention, the samples can be scanned using various techniques (including high throughput NMR and MRI), manipulated, and stored in the well plates.

Figure 2:
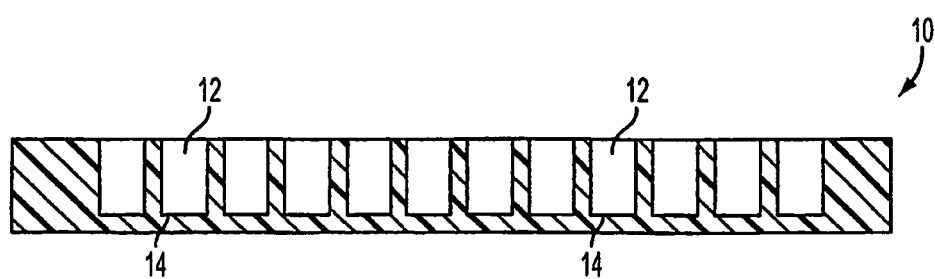
FIG. 2 is a cross-sectional view of the assay plate of FIG. 1, taken along the line II-II of FIG. 1.
Figure 3:
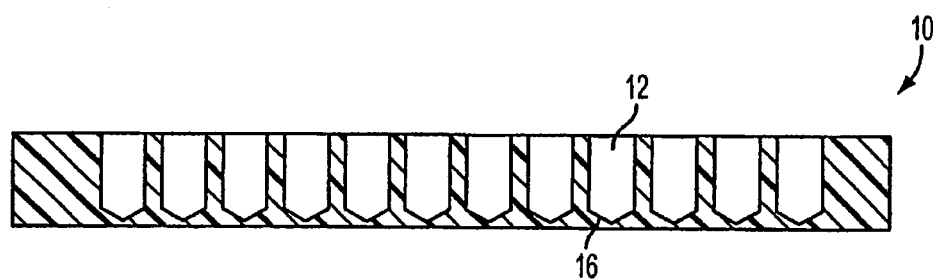
FIG. 3 is a cross-sectional view of an alternative embodiment of the assay plate of FIG. 1, taken along the line II-II of FIG. 1, wherein the wells have a substantially conical bottom surface.

As shown in the cross-sectional view of FIG. 2, the wells 12 may have substantially flat bottom surfaces 14. The flat bottom surfaces 14 can maximize the filling of the imaging voxels. They can also facilitate optical scanning from below the plate. Flat bottom wells 12 may be advantageous when scanning homogeneous samples (e.g., solutions and suspensions), where it is important to eliminate the meniscus from the slice of the sample being scanned, and still scan the largest amount of the sample possible. Alternatively, as shown in FIG. 3, the wells 12 may have cupped bottom surfaces, for example, substantially conical bottom surfaces 16. The cupped bottom surfaces may assist in concentrating certain particles at the bottom of the well. This may be advantageous, for example, when performing heterogeneous assays, such as those involving nanoparticles attached to, located in, or otherwise associated with cells or other biological materials, because concentration of the magnetic nanoparticles, for instance by centrifugation of the plate, intensifies the contrast created by the nanoparticles. This allows smaller numbers of magnetic nanoparticles to be detected (i.e., it improves the detection limit for the nanoparticles and the analyte to which they are bound). As an alternative to the conical bottom surface shown in FIG. 3, the wells 12 may have stepped bottom surfaces or rounded bottom surfaces. Rounded bottom surfaces (shown, e.g., as 16" in FIG. 14) are preferred when the samples include live cells.

As discussed above, differences between the magnetic susceptibility of the assay plate and the samples located in the wells can create a distortion of the magnetic field near each sample and between the wells. This distortion can reduce the performance of the scan to the point that it becomes impossible, for example, to detect magnetic particles in a MRI image, or to resolve NMR spectral lines. In order to reduce and/or eliminate this inhomogeneity in the magnetic field, the assay plates 10 can be constructed of a material (or blend of materials) that exhibits a bulk magnetic susceptibility that is substantially similar or matched to the bulk magnetic susceptibility of the samples. For example, the bulk magnetic susceptibility (the "$\chi$ value") of the assay plate 10 can be matched to the $\chi$ value of one or more of the samples. This can be particularly advantageous when all samples have a similar magnetic susceptibilities, both from well to well and from plate to plate, such as in quality control screening. However, it is also possible that the $\chi$ values will differ from well to well. In this case, the $\chi$ value of the plate can be matched to the average $\chi$ value of the samples or groups of samples. Alternatively, the $\chi$ value of the plate can be matched to the $\chi$ value of just one of the samples.

When referring to the bulk magnetic susceptibility, or $\chi$ value, of a sample, it will be understood to mean the $\chi$ value of the entire content of a well, excluding any kind of cap or stopper. In practice, the bulk magnetic susceptibility of a solution is typically dominated by the $\chi$ value of the solvent, in which case the $\chi$ value of the plate will typically be matched to the $\chi$ value of the solvent. However, the $\chi$ value of the plate can alternatively be matched to both the $\chi$ value of the solvent and the $\chi$ value of the solute. In the case where the sample is a pure substance (e.g., a pure liquid or neat liquid), the bulk magnetic susceptibility will be understood to mean that of the pure substance itself. In the case where the sample is a tissue, the bulk magnetic susceptibility will be understood to mean that of the tissue itself. One of ordinary skill in the art will understand that the bulk magnetic susceptibility may vary from well to well, even when analyzing similar or identical samples.

Matching the susceptibilities of the plates and the samples may in some instances eliminate the need for "shimming" the magnetic field to correct inhomogeneities introduced by magnetic susceptibility mismatches. One of ordinary skill in the art will recognize, however, that shimming may still be necessary to correct inhomogeneities caused by imperfections in the magnet of the MRI scanner. However, these inhomogeneities tend to be linear and relatively easy to shim, whereas inhomogeneities typically caused by magnetic susceptibility mismatches in multi-well plates (e.g., differences between samples, walls, and air in large numbers of wells) tend to be complex and very difficult to shim.

Several commercially available polymers exhibit bulk magnetic susceptibilities that are substantially similar to those of common NMR sample solvents. Table A, below, shows the bulk magnetic susceptibilities for selected polymers (rows one and two) and sample solvents (columns one and two) in cgs units. The remaining entries show the percentage difference between the polymer and the solvent.

TABLE A

| NMR Sample Solvent | Polymer | PI | PEI | PPS ® | PEEK ® |
|---|---|---|---|---|---|
| | $\chi/-\chi_c$ | 0.71 | 0.71 | 0.73 | 0.74 |
| DMSO | 0.68 | 4% | 4% | 7% | 8% |
| CHCl$_3$ | 0.74 | −4% | −4% | −1% | 0% |
| D$_2$O | 0.70 | 1% | 1% | 4% | 5% |
| H$_2$O | 0.72 | −1% | −1% | 1% | 3% |

The necessary degree of matching between the magnetic susceptibility of the plate and the magnetic susceptibility of the sample can depend on many factors. Some of these factors can include, for example: the configuration of the multi-well plate (e.g., the shape and arrangement of the wells, whether air-gaps are present between wells, etc.); the configuration of well-caps being used, if any; the configuration of the MRI, NMR, or other scanning equipment being used; the amount of samples being analyzed in the well-plate, the range of $\chi$ values of the samples being analyzed (where different samples are being analyzed at one time); and the sensitivity of the application. In some exemplary embodiments, a match of about 2% or less is generally considered "substantially similar" or "matched." In some more sensitive embodiments, a match of about 1% or less is generally considered "substantially similar" or "matched."

Below is a list of other materials that may be suitable for susceptibility-matched well-plates:

| Materials |
|---|
| Polychlorotrifluoroethane (Kel-F) |
| Polypropylene (PP) |
| Polystyrene (PS) |
| Polytetrafluoroethane (PTFE, Teflon) |
| Polyimide (Vespel) |
| Fiberglass (G-10 Garolite) |
| Machinable glass-ceramic (Macor) |
| Yttria-doped zirconia ceramic |
| Pyrex 7070 electrical-grade glass |
| Glass-filled PEEK |
| Polycarbonate (Lexan) |
| Polyacetal (Delrin) |
| Polyethylene (PE) |
| Silicone rubber (Dow Corning 96-083) |
| Alumina ceramic |

Below is a list of other solvents that may be suitable for use in susceptibility-matched applications:

| Solvents |
| --- |
| Acetone |
| Benzene |
| Chloroform |
| Ethanol |
| Methanol |
| Toluene |
| Glycerol |
| Methyl ethyl ketone |
| Trichloroethylene |
| Carbon disulfide |
| Cyclooctane |
| Cyclohexane |
| Dioxane |
| Isopropyl alcohol |
| Diethyl ether |

Matching of the magnetic susceptibilities of the plate and samples can be performed empirically, e.g., using known $\chi$ values for the sample and/or plate material. Alternatively, the susceptibility values can be matched through a calibration process. For example, the $\chi$ value of the sample and/or a plurality of plates can be determined using known techniques and equipment. Then, the plate having the closest $\chi$ value to that of the sample can be chosen for use. Alternatively, the calibration process can rely on a combination of empirical data (e.g., lookup tables) and measured data, including already published values. Additionally or alternatively, semi-empirical formulae may be used to estimate the $\chi$ value of various solutes and solutions, mixtures of solvents, and mixtures of plate materials. Additionally or alternatively, a plurality of plates and samples can be scanned together and checked for disturbances in the magnetic field until a match is found that eliminates any such disturbances to an acceptable level.

The assay plate 10 can also be constructed of a blend of one or more materials to obtain a desired bulk magnetic susceptibility. For example, the assay plate 10 can be constructed from a blend of two or more of the above-listed polymers in Table A. Additionally or alternatively, additives may be added to the material of the plate to adjust the $\chi$ value to match that of the sample. For example, metal oxides, such as CuO could be added to the material to adjust its $\chi$ value. According to another exemplary embodiment of the invention, the solvent could be modified to match the $\chi$ value of the plate.

The polymers listed above in Table A are commercially available under the following tradenames: ULTEM® (polyetherimide, also known as PEI), RYTON® (polyphenylene sulfide, also known as PPS), PEEK® (polyetheretherketone), and AURUM® (polyimide, also known as PI). ULTEM® is particularly suited for the assay plate 10 because it is transparent, autoclavable, heat-resistant and impervious to strong acids and bases. The transparency of ULTEM® is particular advantageous because it facilitates identification and removal of air bubbles within the wells. It also allows the plate to be scanned optically. The plates may also be suitable for scanning by a scintillation counter for radioactive labels in the samples. One of ordinary skill in the art will appreciate that assay plate 10 may alternatively be made of other materials, be they polymers or non-polymers. Ceramics, such as zirconia, are one example of other materials that may be used. Glasses, such as high-purity glass, are another example. Composites such as fiberglass, glass-filled Teflon, and carbon fiber are other examples.

Plate 10, and any well-caps that may be used, are preferably made from a material that is substantially impervious to the sample and any media it may be located in, so that the sample and/or media cannot diffuse into the plate 10. The polymers listed above in Table A are believed to be substantially impervious to many known solvents and samples. Plate 10 may also be coated to assist in preventing adhesion of the samples to the plate, and/or to prevent the plate from absorbing the sample. The material of plate 10 may be optimized to be chemically compatible with the samples, to minimize water absorption, or to be thermally conductive. The material of plate 10 may also be optimized to eliminate background signals for the nucleus of interest, prevent air bubble adhesion, improve optical transmission, and reduce light scattering for optical co-imaging.

Figure 4:
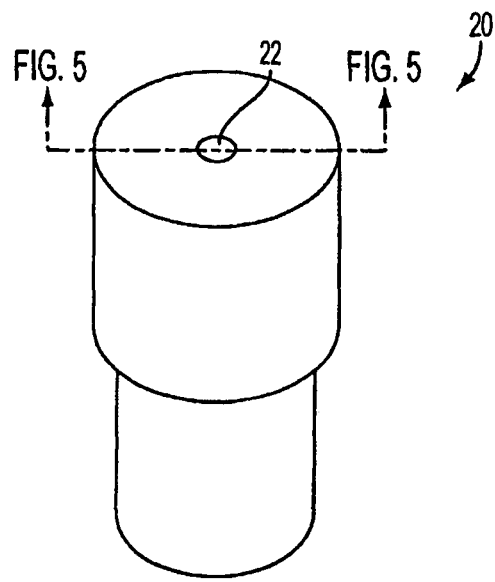
FIG. 4 is a perspective view of an exemplary cap for use with an assay plate according to the present invention.
Figure 5:
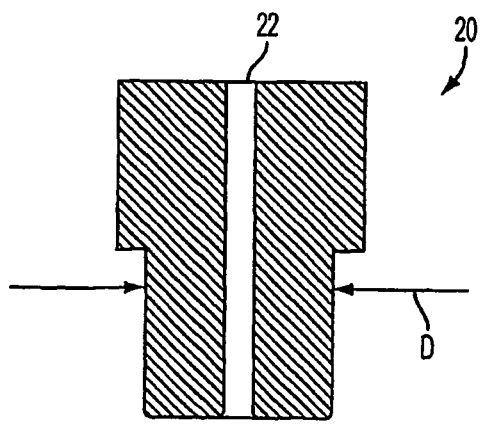
FIG. 5 is a cross-sectional view of the cap of FIG. 4, taken along the line V-V of FIG. 4.

Referring to FIGS. 4 and 5, an exemplary embodiment of a cap 20 according to the present invention is shown. A plurality of the caps 20 can be used to plug the wells in the assay plate 10. Accordingly, cap 20 should have a portion with a cross-section that compliments that of the wells. For example, cap 20 can have a circular cross-section with a diameter D (shown in FIG. 5) that is equal to or slightly smaller than that of the wells, allowing cap 20 to fit snugly within one of the wells 12. Cap 20 can be constructed of a material, or a blend of materials, having a $\chi$ value that is substantially similar to that of the sample and/or to that of the assay plate 10. For example, the cap 20 can be constructed from one or more of the polymers listed above in Table A, although other materials are possible. Preferably, the cap 20 and the assay plate 10 are made of the same material or blend of materials.

Cap 20 can include one or more vent holes 22. In the embodiment of FIGS. 4 and 5, cap 20 includes one centrally-located vent hole 22. The vent hole 22 allows any air located in the well 12 (and possibly a small amount of the sample) to be evacuated upon full insertion of the cap 20 into the well 12. Removing any air trapped in the well is particularly beneficial, because the air-sample interface normally causes a large distortion in the magnetic field in the vicinity of the sample, and introduces distortions into the scan (e.g., it reduces the resolution of NMR spectra, and worsens the detection limit for magnetic nanoparticles). When the assay plate 10 and caps 20 are susceptibility-matched to the sample, and air is eliminated from the well 12 via the vent hole 22, the sample is completely surrounded on all sides by materials having $\chi$ values matched to that of the sample. This greatly reduces disturbances in the magnetic field around the samples, and maximizes spectral resolution in NMR spectroscopy, and optimizes the detection limit for magnetic nanoparticles in MRI imaging. The plate/cap configuration according to the present invention can largely eliminate the effects of mismatched susceptibilities at the air-sample, plate-sample, and/or plate-air interfaces that are common with prior art designs. According to an alternative embodiment, vent hole 22 can be eliminated by forming the cap from a wetted porous, susceptibility-matched material, such as plastic, sponge, or porous ceramic (e.g., zirconia).

Figure 6:
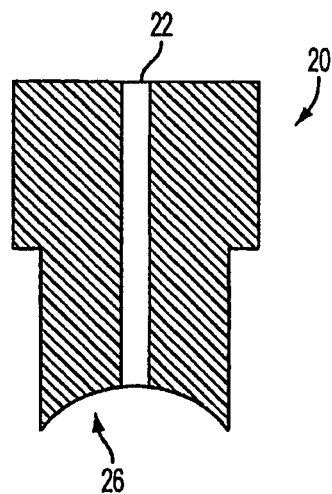
FIG. 6 is a cross-sectional view of an alternative embodiment of the cap of FIG. 4, taken along the line V-V of FIG. 4, wherein the cap has a substantially hemispherical lower surface.

Referring to FIG. 6, an alternative embodiment of cap 20 is shown. According to this embodiment, the cap has a lower surface 26 that is concave, and preferably, hemispherical. The concave lower surface 26 can act as a funnel that facilitates removal of air bubbles from the well through the vent hole 22. Furthermore, when used in conjunction with a hemispherical well, the cap and well can compliment one another to form a spherical well, such as described in more detail below. One of ordinary skill in the art will appreciate that lower surface 26 can have other shapes that facilitate removal of air bubbles, such as conical, or other shapes that eliminate sharp edges where bubbles might adhere.

Figure 7:
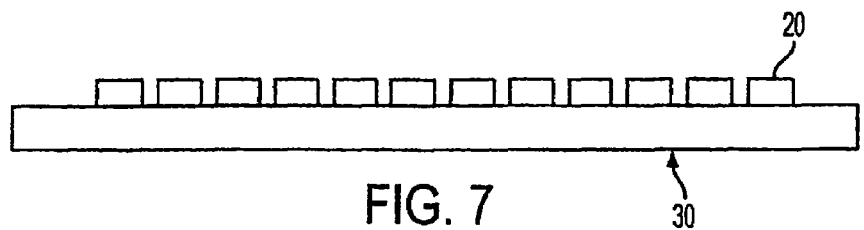
FIG. 7 is a side view of an exemplary cap mat according to the present invention.
Figure 8:
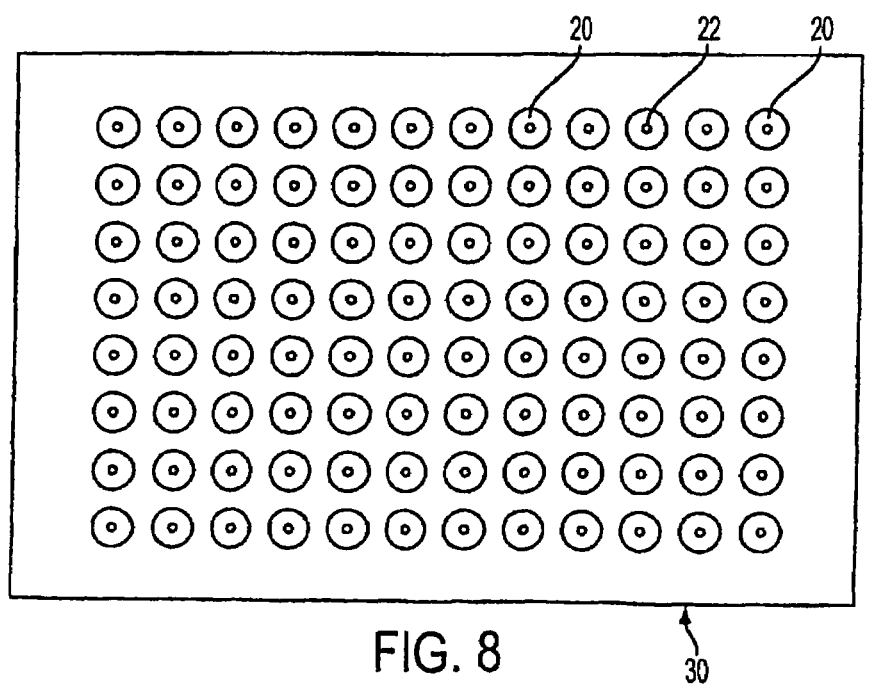
FIG. 8 is a top view of the cap mat of FIG. 7.

Referring to FIGS. 7 and 8, a plurality of caps 20 can be interconnected to form what is known in the art as a "cap mat."

A cap mat 30 allows some or all of the wells 12 in an assay plate 10 to be plugged in a single step, for example, robotically, thereby eliminating wasted time due to individually capping each well 12. This is particularly useful when working with assay plates 10 having numerous wells. According to an alternative embodiment, known as a "strip mat" the mat may include a strip of caps 20 arranged to plug all of the wells in a certain row or column of the assay plate, in which case multiple strip mats would be used to cover the entire assay plate. Conventional robotic equipment can be used to install a cap mat or strip mat onto an assay plate. When samples are stored in the assay plate 10, it may be advantageous to seal off the vent holes 22, for example, by applying a thin layer of material over each of the vent holes 22. This helps prevent evaporation and/or contamination of the samples during scanning, manipulation, and storage. In the case where a cap mat is used, a continuous layer of material may be placed on the top surface of the cap mat.

According to an alternative embodiment of the present invention, the assay plate and the caps can be formed as an integral unit. For example, as shown in the cross-sectional view of FIG. 9, each well 12' can have a cap 20' that is integral with the plate 10', that is, non-removable once the plate is manufactured. The caps 20' can be co-formed with the plate 10', for example, during an injection molding process, or an investment molding process. Alternatively, the caps 20' can be formed separately from the plate 10' and permanently attached thereto, for example, by bonding the caps 20' in each well 12'. According to yet another variation, the plate 10' can comprise two or more layers, e.g., an upper layer and a lower layer, that are permanently bonded together. In the case where the caps 20' are integral with the plate 10', the wells 12' preferably have a vent hole 22' that is large enough in diameter to allow air and/or liquid to escape through the vent hole 22' as the sample is being introduced into the well 12', for example, around the sides of a needle. Alternatively, each cap 20' can have at least one "filler hole" through which the sample can be introduced, and at least one "vent hole" through which air and/or the sample can escape.

Figure 9:
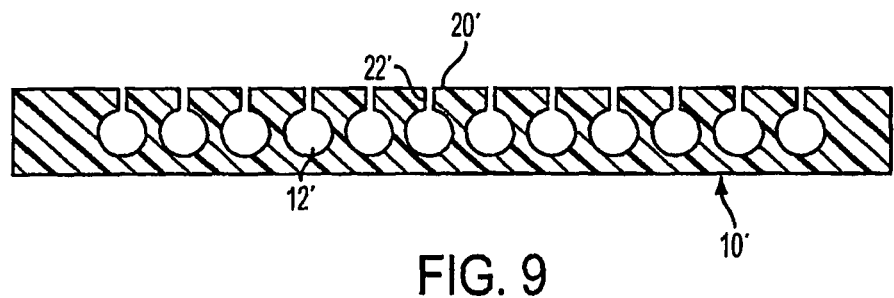
FIG. 9 is a cross-sectional view of an alternative embodiment of the assay plate of FIG. 1, taken along the line II-II, wherein the plate has substantially spherical wells.

Still referring to FIG. 9, the wells 12' in plate 10' can be substantially spherical in shape. Plates with non-integral caps can also have spherical-shaped wells, for example, if the well itself has a hemispherical bottom surface and the cap has a mating hemispherical surface. See the cap 20 with spherical undersurface shown in FIG. 6. Spherical-shaped wells may be advantageous for several reasons. For one, magnetic field gradients within each well may cancel each other out when the wells are spherical in shape, thereby reducing or eliminating the deleterious effects of gradients caused by residual mismatched susceptibilities. However, a high degree of sphericity is typically required to obtain this canceling-out effect. The spherical-shaped wells may also help eliminate air bubbles in the wells, by eliminating any sharp corners or surfaces on which air bubbles can get trapped. This is particularly advantageous due to the large distortions in the magnetic field typically caused by bubbles and the associated air-sample interface. Once loaded with samples, the plates can be manipulated to further reduce air bubbles. For example, the plates can be subjected to a slight vacuum (e.g., placed in a bell jar), centrifuged, and/or sonicated.

Figure 16:
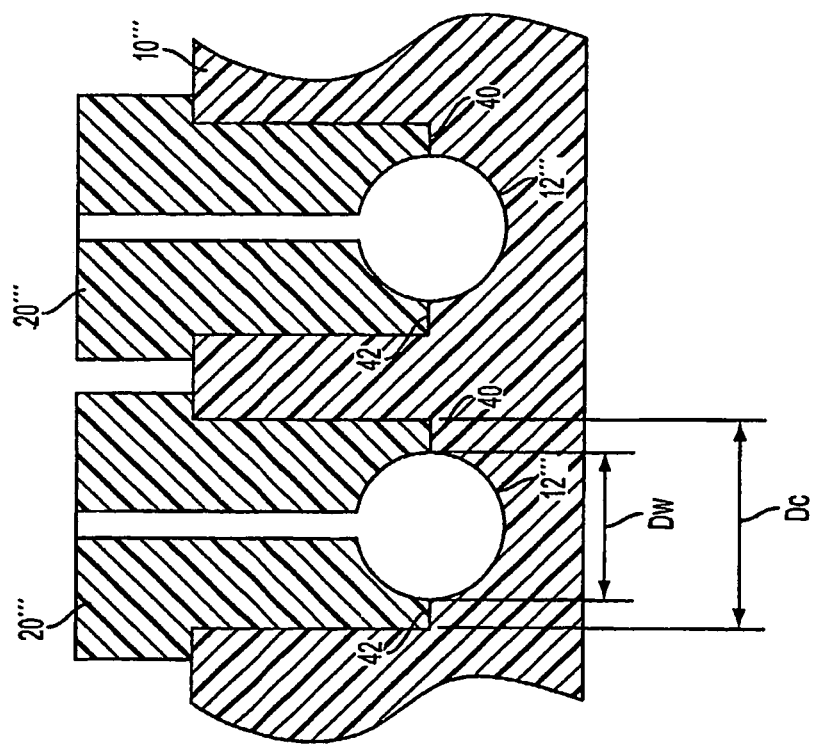
FIG. 16 is a partial cross-sectional view of an alternative embodiment of the assay plate of FIG. 1, taken along the line II-II of FIG. 1, in combination with well caps, wherein the wells have substantially round or hemispherical bottom surfaces, and the caps have corresponding substantially round or hemispherical surfaces.

Referring to FIG. 16, another embodiment of an assay plate and well caps according to the present invention is shown. The plate 10''' and caps 20''' are shown in partial cross-sectional view (e.g., along line II-II of FIG. 1). As shown in FIG. 16, the plate 10''' and caps 20''' can define substantially spherical wells for the samples. More specifically, each of the wells 12''' in the plate can have a substantially round or hemispherical surface, as shown. Each of the caps 20''' can have a corresponding lower surface 26''' with a substantially round or hemispherical depression. To facilitate manufacturing of the plate 10''' and/or the caps 20''', a step 40 can surround each of the wells 12'''. In addition, a matching rim 42 can surround the depression in the lower surface 26''' of each of the caps 20'''. Each step 40 and corresponding rim 42 can mate to form a leak-tight face seal, provided the respective cap 20''' can be pushed down far enough to facilitate this contact.

As shown in FIG. 16, the diameter Dw of each well 12''' can be smaller than the diameter Dc of each corresponding cap 20'''. This arrangement can facilitate manufacturing (e.g., machining, molding, etc.) of the hemispherical depression in lower surface 26''' of each of the caps 20''' since the need for a fragile, sharp edge along the plug rim 42 may be eliminated.

According to the exemplary embodiment of FIG. 16, the caps 20''' can be pushed into each well 12''' after filling the plate 10''' with samples, or, alternatively, they can be force-fit or solvent-welded to the plate before adding samples. In the latter case, samples can be introduced through the vent hole 22''' in each plug 20''' using a needle, cannula, tube, or other device attached to a syringe, pump, robotic sample dispenser, or other filling device.

Figure 24:
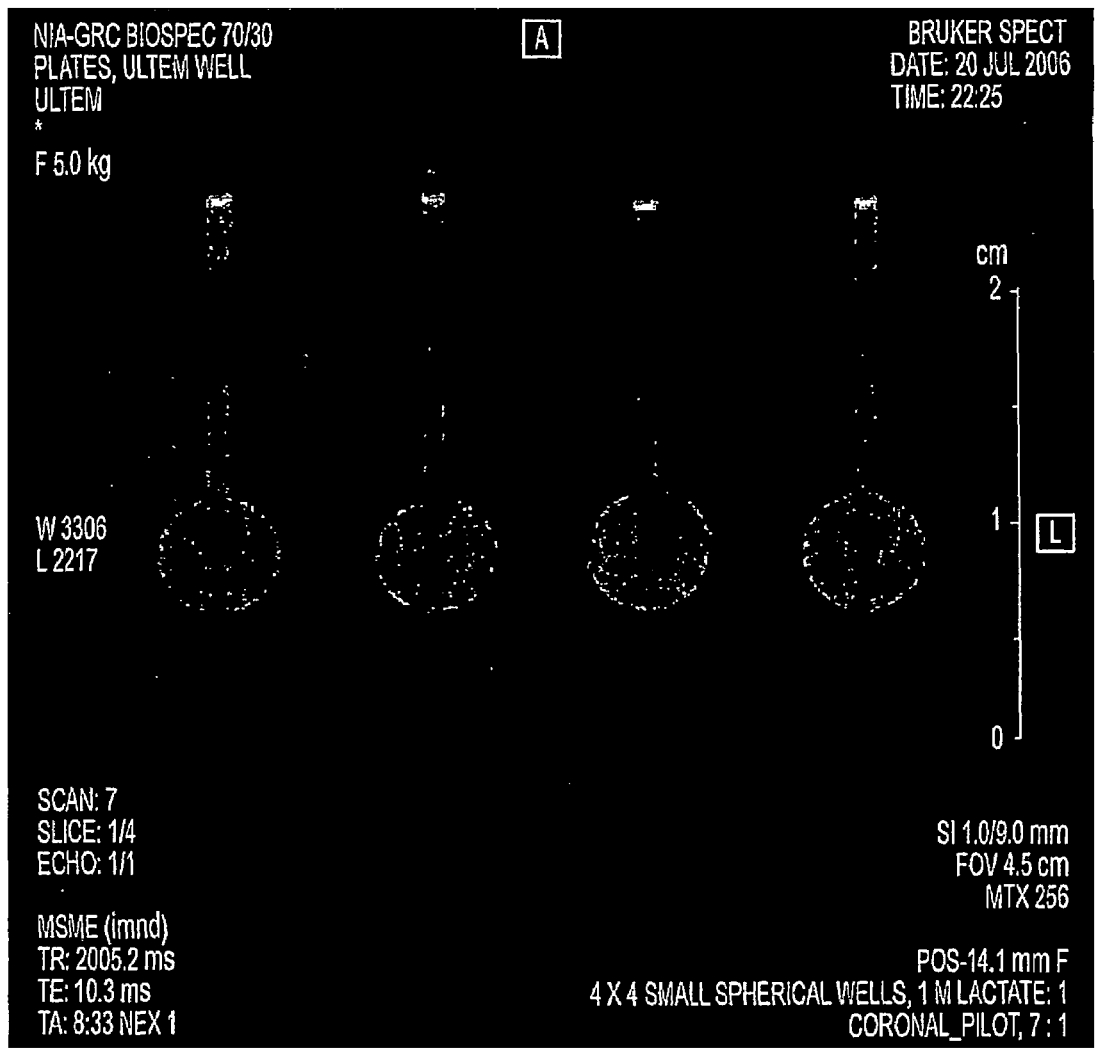
FIG. 24 depicts an MRI image of a susceptibility-matched plate and plugs of FIG. 16, taken perpendicular to the face of the plate.

An example demonstrates some of the benefits of the exemplary embodiment of FIG. 16. Referring to FIG. 24, shown is an MRI image of a 4 well×4 well plate and cap set designed according to FIG. 16. The wells are filled with 1 M lactic acid solution. The image comes from a slice taken perpendicular to the face of the plate. As shown in FIG. 24, the wells clearly appear quite circular and there is no evidence of sample leakage at the rim-step interface or around the body of each cap. The meniscus is displaced far above the wells, as seen near the top of the image. This example demonstrates that the exemplary embodiment of FIG. 16 can easily produce a very good approximation of spherically-shaped wells without fluid leakage.

Figure 17:
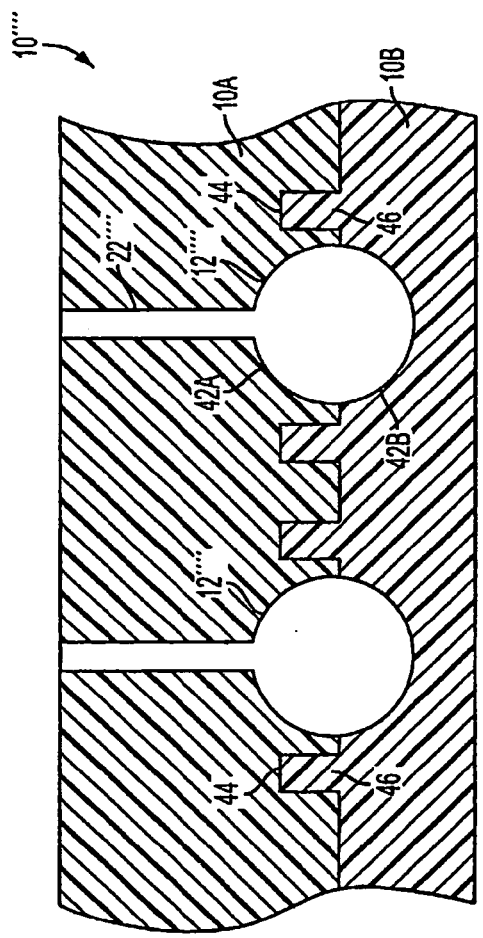
FIG. 17 is a partial cross-sectional view of an alternative embodiment of the assay plate of FIG. 1, taken along the line II-II, wherein the plate has substantially spherical wells.
Figure 18:
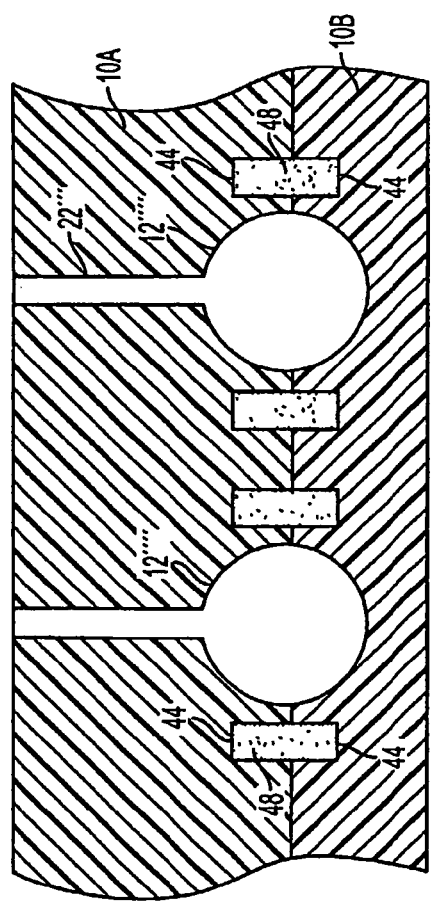
FIG. 18 is a partial cross-sectional view of yet another alternative embodiment of an assay plate similar to that shown in FIG. 17.

According to another exemplary embodiment, the assay plate can comprise upper and lower layers of material that are attached together, for example, by bonding, fasteners, or other known techniques. The sample wells may be defined by cooperating depressions in the adjacent surfaces of the upper and lower layers. Exemplary embodiments of multi-layer plates are depicted in FIGS. 17-18, wherein each figure is a partial cross-sectional view taken along the line II-II of FIG. 1. Referring to FIG. 17, the plate 10'''' can comprise an upper layer 10A and a lower layer 10B. The upper layer 10A and lower layer 10B can be fastened together using screws, rivets, or other structures known in the art. Alternatively, the upper layer 10A and lower layer 10B can be bonded together using glue, ultrasonic welding, or other techniques known in the art. The upper layer 10A and the lower layer 10B can include cooperating depressions 42A, 42B that together define the sample wells 12''''. In the exemplary embodiment shown, the wells 12'''' are substantially spherical, in which case the cooperating depressions 42A, 42B are each substantially hemispherical, however, other shapes and configurations of wells are possible with the multi-layer plates, such as round, square, etc. In order to prevent leakage from each of the individual wells 12'''', a tongue-and-groove seal may be provided between the upper layer 10A and the lower layer 10B around each of the wells 12''''. For example, each tongue-and-groove seal may be substantially circular (when viewed from above) and circumscribe one of the wells 12''''. Referring to FIG. 17, the upper layer 10A can include a substantially circular recess or groove 44 located around each of the wells 12'''', and the lower layer 10B can include a corresponding circular projection or tongue 46 located around each of the wells 12''''. The respective tongues 46 and grooves 44 can cooperate to form a liquid-tight seal around each of the wells 12''''. Although FIG. 17 shows the tongue portion 46 formed on the lower layer 10B and the groove portion 44 formed on the upper layer 10A, the opposite arrangement is also possible.

Referring to FIG. 18, according to an alternative embodiment, a sealing ring can be provided between the upper layer 10A and the lower layer 10B around each of the wells 12''''. For example, the upper layer 10A can include a recess 44 surrounding each of the wells 12'''', and the lower layer 10B can include a corresponding recess 44 around each of the wells 12''''. A circular sealing ring 48 can be located in the common space defined by each pair of recesses. The sealing ring can be made from the same material as the upper and lower layers 10A, 10B themselves. Alternatively, the sealing ring can be made from a different material that is susceptibility matched to the upper and lower layers 10A, 10B, for example, an elastomeric material. In the embodiments described above, the tongue, groove, and/or sealing ring need not have a rectangular cross-section. For example, round, elliptical, or diamond-shaped cross-sections may be used as well.

Figure 19:
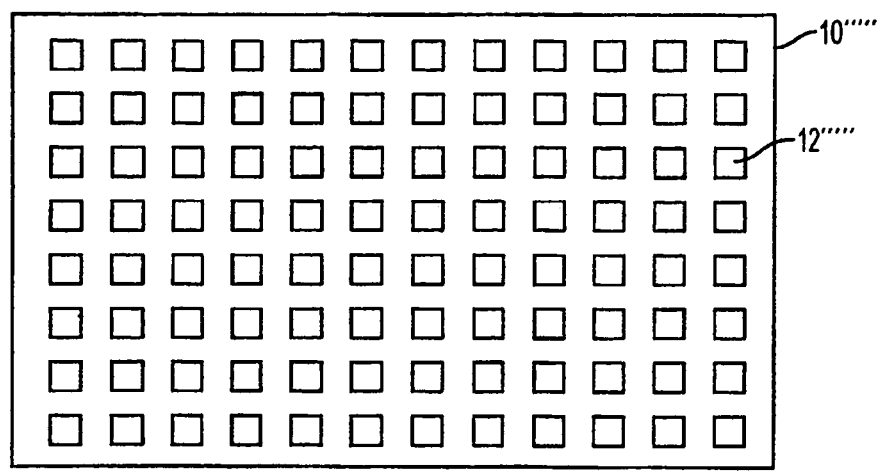
FIG. 19 is a top view of an alternative embodiment of the assay plate of FIG. 1, wherein the wells of the assay plate are square or rectangular box-shaped.

Referring to FIG. 19, another embodiment of an assay plate is shown. According to this exemplary embodiment, plate 10'''' can have rectangular, or square wells 12'''''. That is, each of the wells 12'''' can be substantially rectangular or square when viewed from the top. All the three dimensions of the well (length, width, height) can be equal, or alternatively, two or more may be different, for example, in a rectangular parallelepiped. The wells 12'''' can have substantially flat bottoms (e.g., similar to what is shown in FIG. 2), such that each well 12'''' approximates a box-shape or cube-shape. One of ordinary skill in the art will appreciate, however, that other bottom shapes are possible, such as stepped, tapered, curved, etc. Plates having rectangular or square wells can be advantageous in several situations. For example, some sequences, such as PRESS and chemical shift imaging (CSI), obtain spectra from square or rectangular voxels, in which case a square or rectangular sample fills the voxels more efficiently than most other shapes. In addition, given an industry-standard spacing of about 9 mm between the centers of adjacent wells 12'''' in either the row or column direction, square wells can fill the available plate area more efficiently than some other shapes, possibly permitting a greater volume of sample to be placed in each well 12'''' without increasing the overall thickness (in the vertical direction) of the plate 10''''. Well caps in various arrangements (e.g., integral, separate, cap mats, strip mats, etc.) may be provided for the square wells 12''''. The well caps can have substantially flat undersurfaces, however, other configurations are possible, such as cupped, stepped, etc. Square, rectangular, and other geometric-shaped wells can have rounded corners where adjacent walls intersect, for example, to prevent bubble entrapment in the corners.

In order to reduce the likelihood of air bubble adhesion, the surfaces of the plate and/or caps can be treated to resist the buildup of air bubbles thereon. For example, the plates and/or caps can be coated to prevent air bubble adhesion. Other possible treatments include applying a large electrical potential across the plate and/or caps to ionize the surface of the material.

Figure 14:
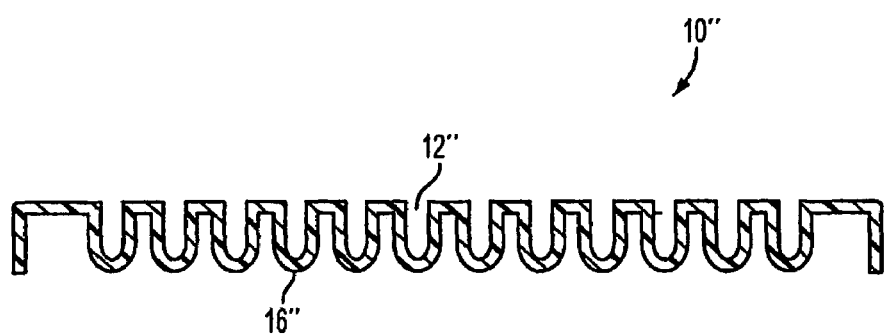
FIG. 14 is a cross-sectional view of an alternative embodiment of the assay plate of FIG. 1, taken along the line II-II of FIG. 1, wherein the wells have a substantially hemispherical or round bottom surface, and wherein air gaps are present between the wells.

The exemplary plates shown in FIGS. 1, 2, 3, 9, and 16-19 have substantially rectangular cross-sections. That is, the plates are solid blocks (of one or more layers of material) having the wells defined therein. This configuration eliminates air spaces between the wells, which can cause magnetic field inhomogeneities. The plates of the present invention are not limited to such a configuration, however. According to an alternative embodiment of the present invention, the undersurface of the plate can have air gaps between adjacent wells 12'', provided the wall thickness of the plate is adequate to provide effective susceptibility matching. As shown in FIG. 14, according to one exemplary embodiment, the undersurface of plate 10'' can follow the contours of the wells. Air gaps between adjacent wells can help facilitate thermal equilibrium for the samples. The plate may be varied between the "block" designs of FIGS. 1, 2, 3, 9, and 16-19, and the design of FIG. 14 to provide the optimal balance between eliminating inhomogeneities and providing adequate thermal equilibrium. In other words, the thickness of the walls around each well can be optimized between very thin (inexpensive, good thermal equilibrium kinetics) and unitary with all other wells.

According to another exemplary embodiment of the present invention, the assay plate can comprise separate rows or columns of wells that attach to a frame. For example, the assay plate can comprise eight separate 12×1 plates that attach to a frame to form a 96 hole plate of conventional size and dimensions. According to this embodiment, at least the individual rows of wells may be susceptibility matched to the samples.

According to an alternative embodiment of the present invention, the susceptibility-matched assay plate could include one or more reader coils wrapped around each of the wells. This may result in increased signal-to-noise ratio.

According to yet another exemplary embodiment, the assay plate could take the form of a slide, for a microscope or similar instrument, and the slide could include an array of microscopic dimples for receiving samples. The slide could further include a covering device, either in the form of a sheet to cover the slide, or miniature caps to plug the dimples. The slide and/or the covering device could be susceptibility matched to the samples. One of ordinary skill in the art will appreciate that the present invention is not limited to any specific size of plate.

The plates and/or caps of the present invention can be particularly advantageous for use in horizontal-bore MRI instruments.

An example demonstrates the advantages of the magnetic susceptibility-matched assay plates of the present invention. MRI images were acquired of two different well plates: a conventional 96-well plate made of polystyrene, and a 16-well susceptibility-matched plate made of ULTEM®. Both plates had wells of the same size, shape, and spacing. Sixteen samples were introduced into each of the plates in the same arrangement, i.e., four rows by four columns. Each sample consisted of 200 micro liters of 10 mM $CuCl_2$ solution in water. Both gradient echo and spin echo MRI images were recorded for each plate using a BRUKER® Biospec 70/30 scanner (a horizontal-bore instrument, analogous to a clinical MRI scanner).

Figure 10A:
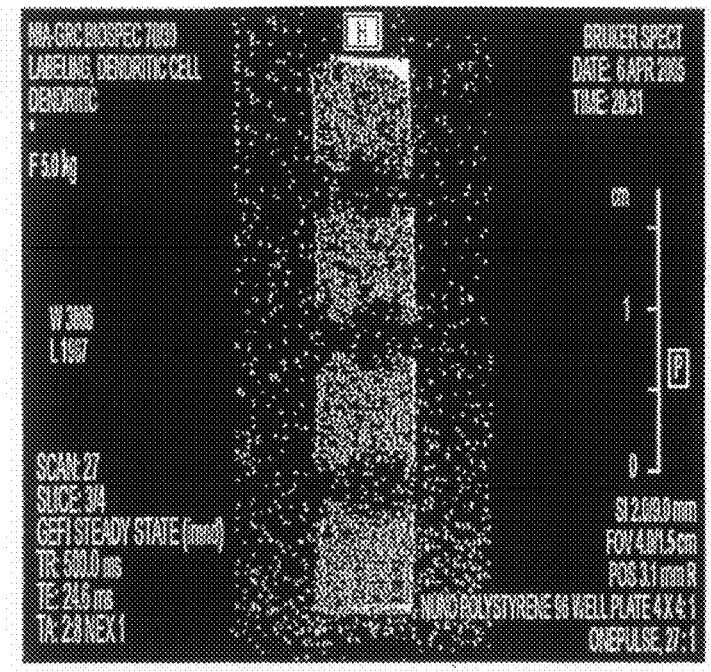
FIGS. 10A and 10B are gradient echo MRI images of the central 16 wells of a conventional polystyrene 96-well assay plate, taken perpendicular to the face of the plate.
Figure 10B:
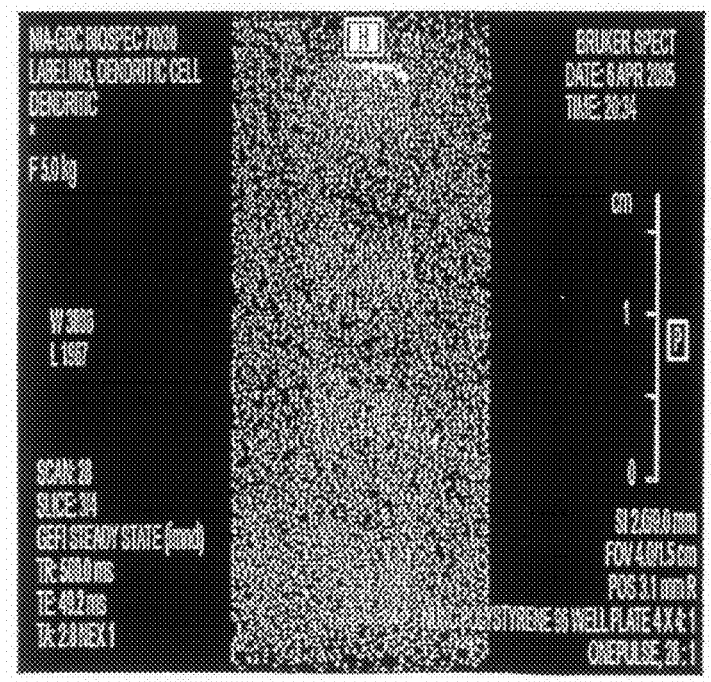
Figure 11A:
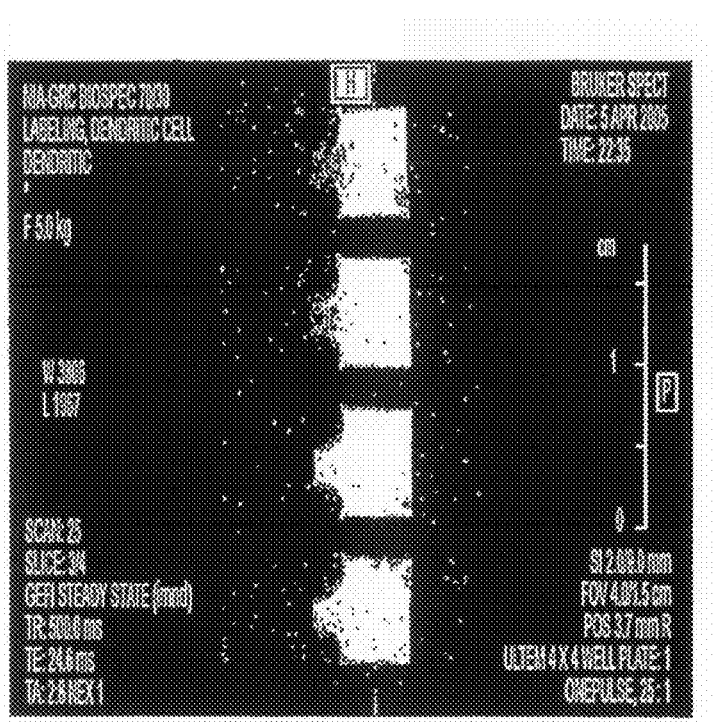
FIGS. 11A and 11B are gradient echo MRI images of a magnetic susceptibility-matched 16-well assay plate of the present invention, taken perpendicular to the face of the plate.
Figure 11B:
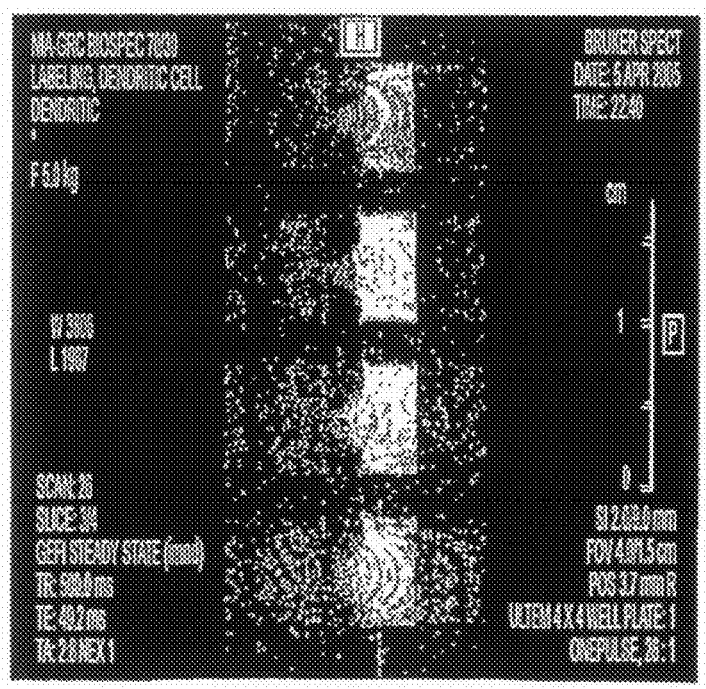

FIGS. 10A and 10B are gradient echo images for four wells in one row of the polystyrene plate, taken perpendicular to the face of the plate. The imagine slice passed through the center of each well. FIGS. 11A and 11B are gradient echo images for the corresponding four wells of the ULTEM® plate, also taken perpendicular to the face of the plate. FIGS. 10A and 11A were taken with an echo time (TE) of 24.6 milliseconds, and FIGS. 10B and 11B were taken with a longer echo time of 49.2 milliseconds. The longer echo times used in FIGS. 10B and 11B generally improve the sensitivity for detecting magnetic particles, however, the longer echo times also increase the sensitivity of the scan to distortions caused by mismatched bulk magnetic susceptibilities.

In FIGS. 10A, 10B, 11A, and 11B, the top of the assay plates are on the left sides of the images. Note that at the same echo times, substantial signal loss and massive distortions in the sides of the wells are visible in the polystyrene plate, yet the ULTEM® plate according to the present invention shows distortions only at the top of each well, where the air-water interface (meniscus) causes residual magnetic field distortions. Clearly, the susceptibility-matched plate eliminates much of the magnetic field inhomogeneity present in the conventional plate, resulting in images with much less distortion and a much greater signal-to-noise ratio. Even using the longer echo time, which makes the image quality more vulnerable to inhomogeneities in the magnetic field, the susceptibility-matched plate resulted in good images. The addition of a susceptibility-matched cap or cap mat (such as described above and shown in FIGS. 4-8) can eliminate the remaining distortion associated with the air-sample interface in each of the wells.

Figure 15:
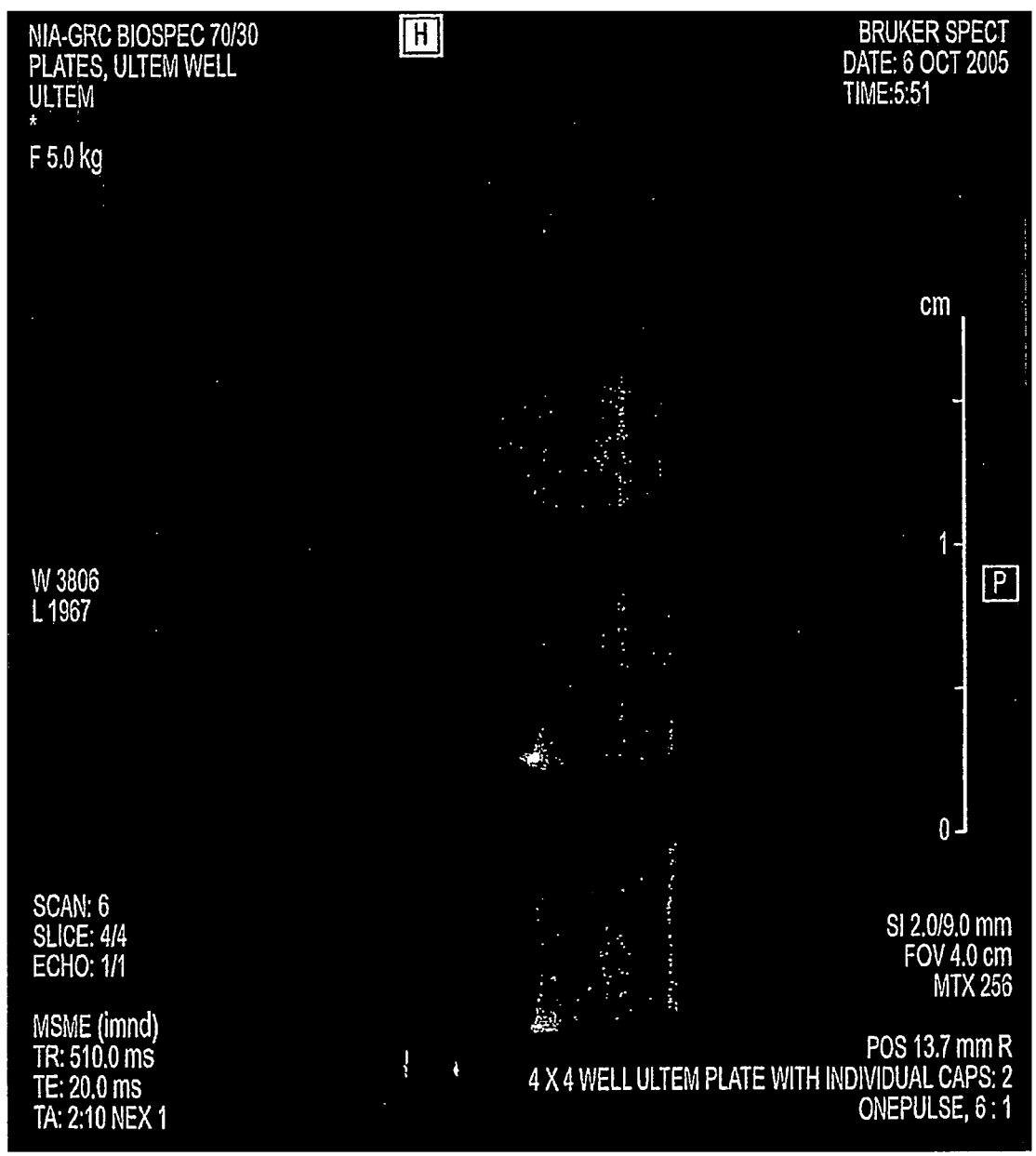
FIG. 15 is spin echo MRI image of a magnetic susceptibility-matched multi-well assay plate of the present invention, taken perpendicular to the face of the plate, with the top two wells capped by caps shown in FIG. 6 and the bottom two wells uncapped.

FIG. 15 is a spin echo MRI image of a 4×4 ULTEM® well plate according to the present invention, taken perpendicular to the face of the plate. The upper two wells have ULTEM® caps installed (according to FIG. 16), while the lower two wells are open. The left side of the image corresponds to the top of the plate. The image was acquired with an echo time of 20 milliseconds. All wells were filled with a 10 mM $CuCl_2$ solution in water. Distortions can be seen around the menisci in the lower two wells. However, in the upper two wells, the wells are straight and undistorted. In the caps, some distortion can be seen at the very top of the liquid in the vent holes, but this is far above where an imaging slice parallel to the face of the plate would typically be taken. Thus, it is apparent that the narrow vent hole moves the meniscus far away from the region of the sample being analyzed.

Figure 12A:
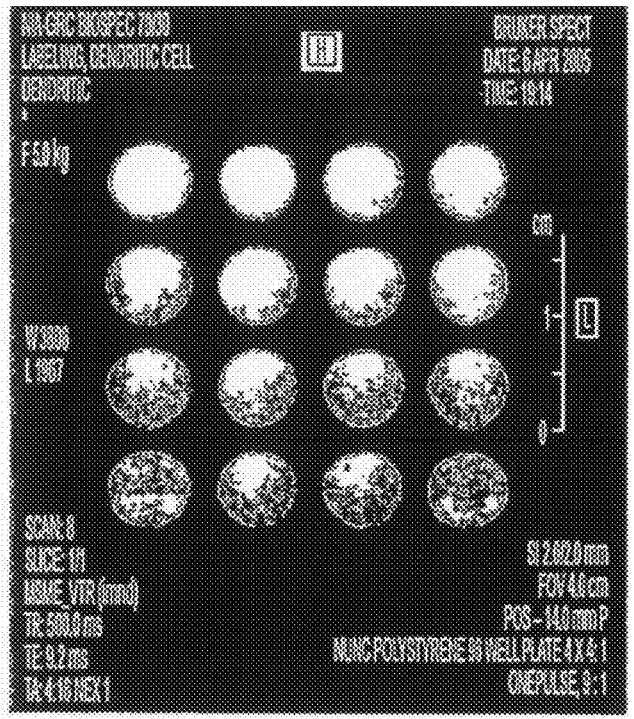
FIGS. 12A and 12B are spin echo MRI images of the conventional polystyrene multi-well assay plate of FIGS. 10A and 10B, taken parallel to the face of the plate.
Figure 12B:
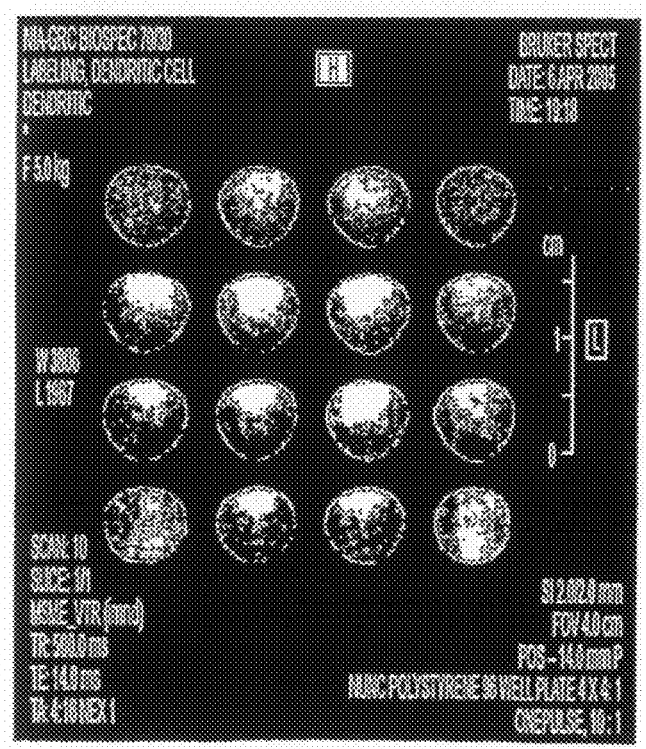
Figure 13A:
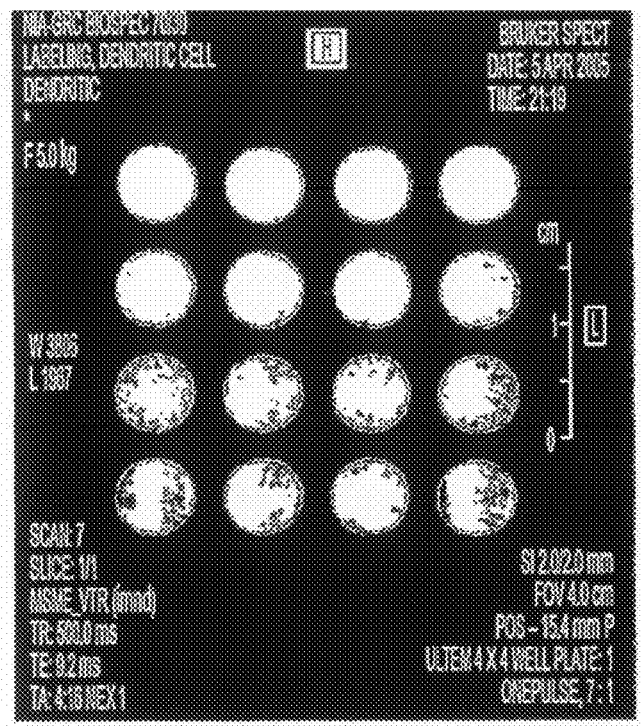
FIGS. 13A and 13B are spin echo MRI images of the susceptibility-matched multi-well assay plate of FIGS. 11A and 11B, taken parallel to the face of the plate, with the imaging slice positioned just above the bottoms of the wells and below the menisci.
Figure 13B:
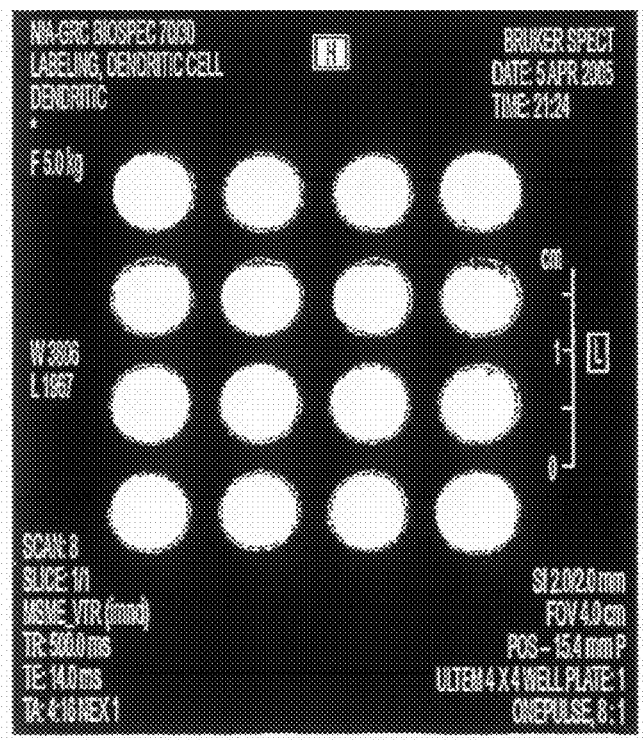

Referring to FIGS. 12A and 12B, spin echo images are shown for the polystyrene plate, taken parallel to the face of the plate, with the imaging slice taken just above the bottom of each well and below the menisci. No caps were used for these images. Corresponding images are shown for the susceptibility-matched plate in FIGS. 13A and 13B, also taken parallel to the face of the plate. FIGS. 12A and 13A were taken with an echo time of 9.2 milliseconds, and FIGS. 12B and 13B were taken with a longer echo time of 14.0 milliseconds.

Although the spin-echo pulse sequence used here is less vulnerable to artifacts associated with magnetic field inhomogeneities than the gradient echo sequence used to produce FIGS. 10 and 11, distortions are clearly seen in the images of the circular wells of the conventional multi-well plate, particularly in FIG. 12B, where a longer TE was used. These oval-shaped distortions are completely absent in the images of the susceptibility-matched plate, again demonstrating that the susceptibility-matched assay plate design eliminates much of the magnetic field inhomogeneity present in the direction parallel to the face of the plate. Thus, even when using the more robust spin-echo sequence, the susceptibility-matched plate of the present invention still improved the image quality as compared to the conventional plate. The improved image quality, as an indicator of B0 field homogeneity, implies improved spectral resolution and detection limits, both for chemical analysis of solutions and for detecting magnetic nanoparticles.

Figure 20A:
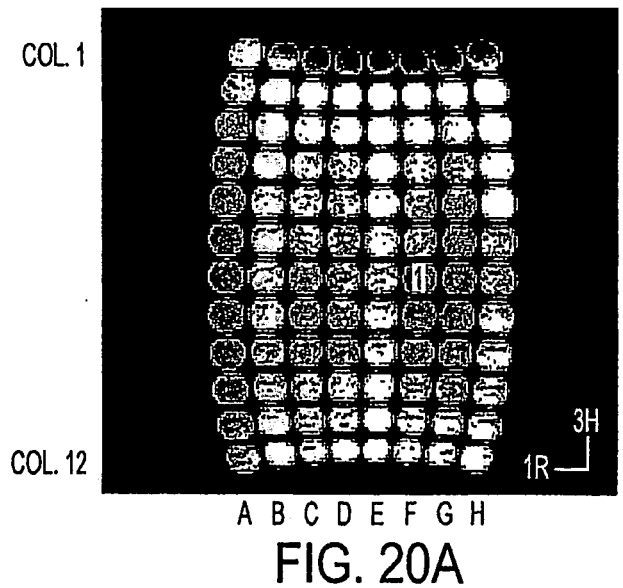
FIG. 20A is a pilot scan of a susceptibility-matched assay plate of the present invention, loaded with three different samples, each sample loaded into multiple wells and rows, the scan taken parallel to the face of the plate, wherein the rows and columns of the plate are identified by numbers and letters, respectively; a typical imaging voxel is shown at well F7.
Figure 20B:
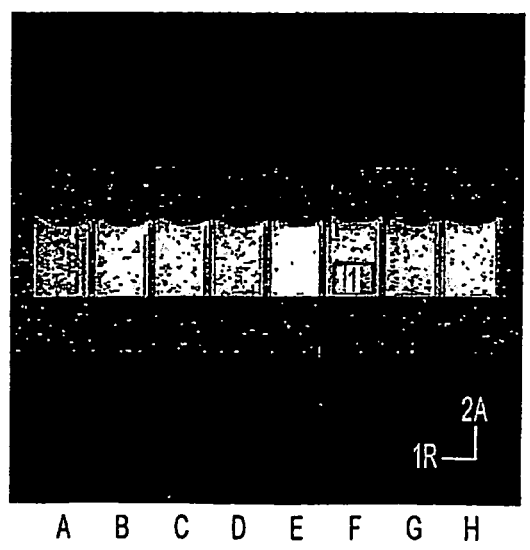
FIG. 20B is a pilot scan of the assay plate shown in FIG. 20A, taken perpendicular to the face of the plate; a typical imaging voxel is shown at well F7.

Another example demonstrates that susceptibility-matched multi-well plates can be used to obtain well-resolved NMR spectra of solutions in each well. A 96-well plate made of ULTEM® according to the present invention was used. The plate had flat-bottomed wells, and no well caps were used. Referring to FIGS. 20A and 20B, rows A, D, and G contained samples of 200 mM L-glutamine having a pH of 5.6; rows B, E, and H contained samples of 1 M L(+)-lactic acid having a pH of about 1.9; and rows C and F contained samples of 90 mM L-phenylalanine having a pH of 6.3. All three compounds were dissolved in undeuterated water. 600 µl of solution was added to each well. Echo times (TE) of 23 milliseconds were used. NMR signals were obtained from a 6 mm×5 mm×5 mm (150 µl) voxel at the bottom of each well.

The PRESS pulse sequence (see Ordidge R. J. et al., 1985 Volume selection for in vivo biological spectroscopy *Magnetic Resonance in Biology and Medicine* (New Delhi: Tata McGraw-Hill) (incorporated herein by reference)) was used to detect signal specifically from a single well at a time. This sequence provides the advantage that instrumental parameters such as magnetic field shimming, excitation frequency, and pulse power calibration can be optimized for each well independently, compensating for inevitable variations in $B_0$ field strength, uncompensated susceptibility differences, and $B_1$ inhomogeneity. This is in contrast to other sequences, such as CSI, in which a single, compromise choice of shim gradients, excitation frequency and RF pulse gains must be made since all wells are scanned at once. As a side benefit, PRESS allows you to compensate for slow drift in the main magnetic field B0 over time since you can measure the NMR resonance frequency each time you scan a new well. With CSI, you have to hope that the field doesn't drift during your experiment or compensate for field drift by hardware, i.e., a field-frequency lock channel. This is a standard feature on vertical-bore NMR instruments but practically unknown on horizontal-bore MRI scanners. Other advantages of PRESS over CSI include much less crosstalk between wells and the ability to see data for wells as they are scanned. CSI requires a very large data matrix to adequately resolve one well from another and you don't get the results until the entire plate is scanned.

The use of undeuterated water as the solvent in the example necessitated the use of water suppression (VAPOR water suppression sequence) to attenuate the very strong signal from water, in order to expose the relatively weaker solute peaks. Water suppression usually works well only when the water peak can be shimmed to a narrow width. For further details on VAPOR, see I. Tkac et al., Magn. Reson. Med., 41(4), 649-656 (1999) (incorporated herein by reference).

Figure 21:
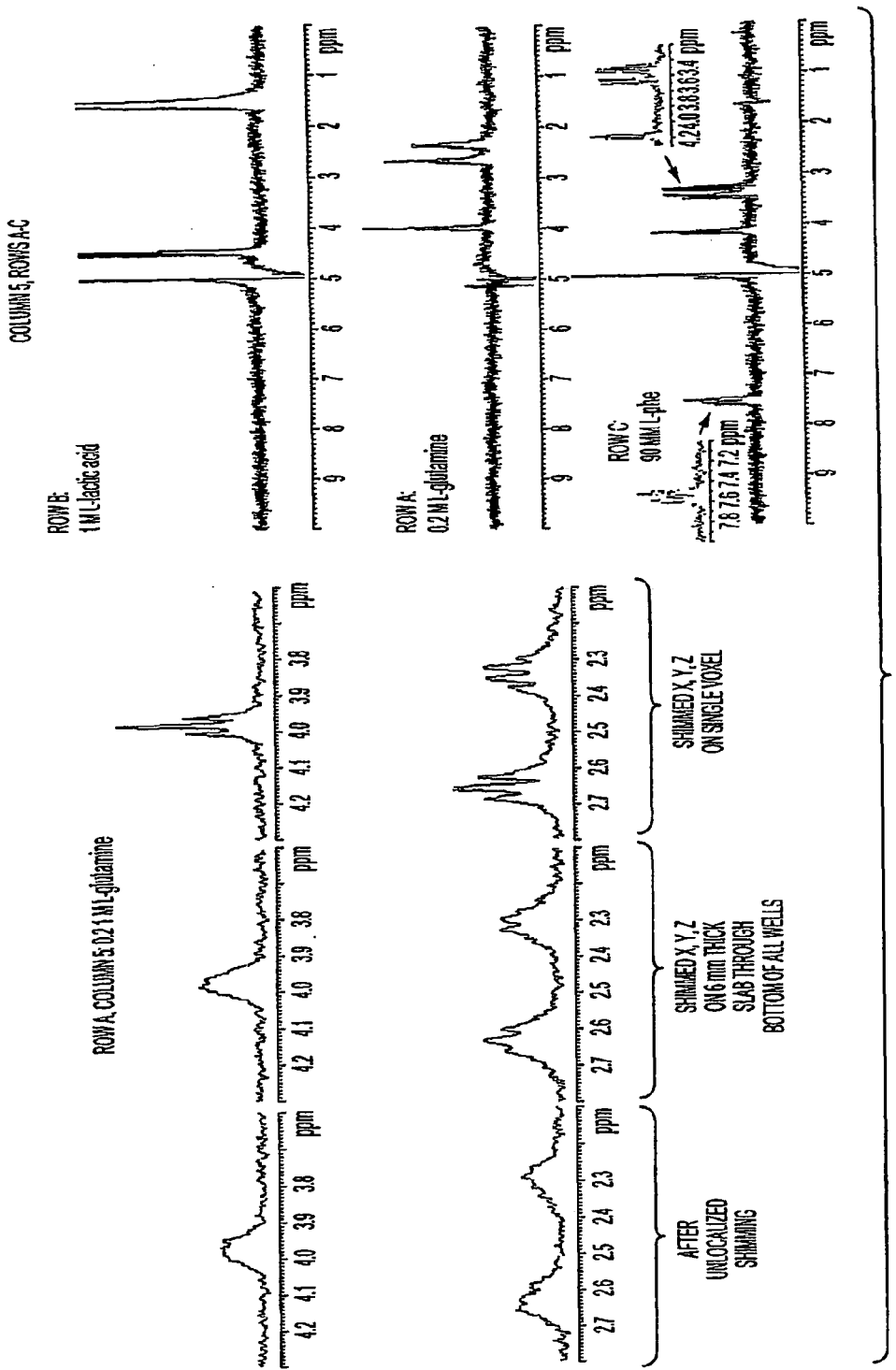
FIG. 21 depicts graphs of localized spectra for various rows and columns of the assay plate of FIG. 20A.
Figure 22:
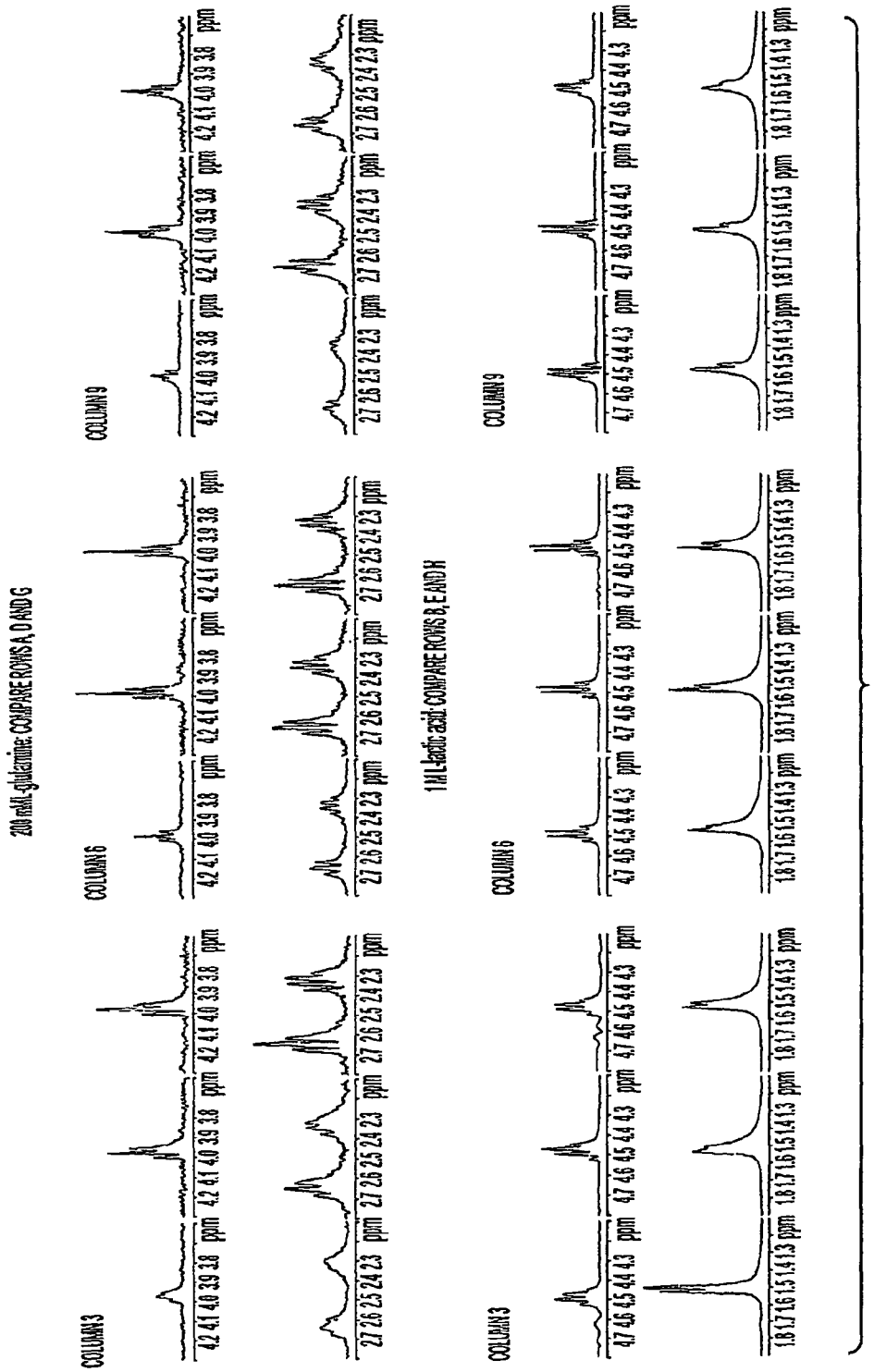
FIG. 22 depicts graphs comparing the spectral resolution versus the well location for the assay plate of FIG. 20A.
Figure 23:
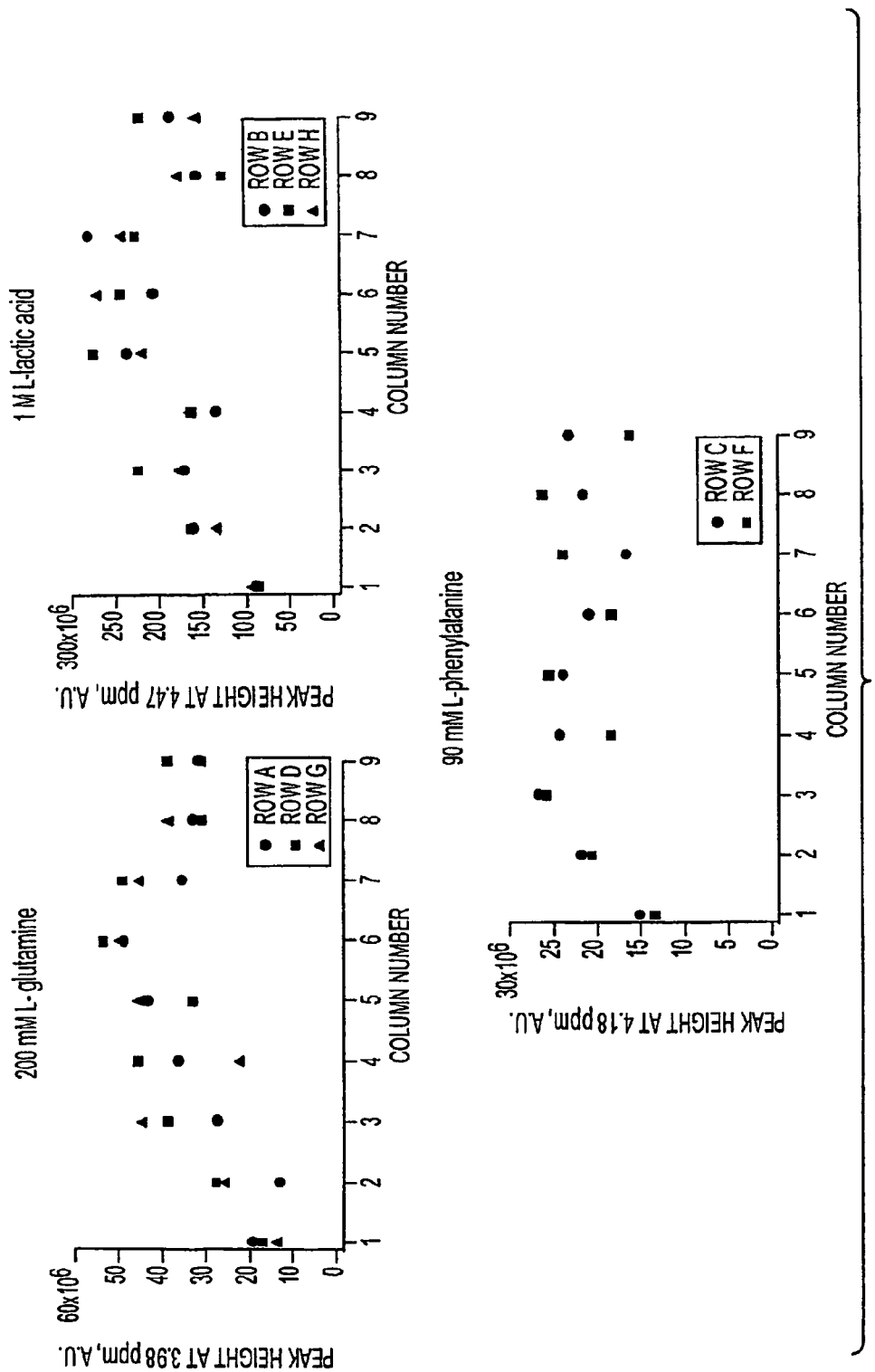
FIG. 23 depicts graphs comparing the spectral peak height versus well location for the assay plate of FIG. 20A.

As shown in FIG. 21, there was no detectable spectral cross-contamination between adjacent wells containing different compounds. For example, compare the spectra for rows A, B, and C. Also, FIG. 21 shows the benefit of being able to shim for each well independently in PRESS (see right column in left panel), as opposed to using a compromise set of shim values for all wells, as would be needed in CSI (see middle column in left panel). As shown in FIG. 22, spectral resolution varied with row and column number across the plate. As shown in FIG. 23, signal-to-noise ratio (proportional to peak heights) varied with row and column number across the plate. FIGS. 21 and 22 reflect some residual $B_0$ and $B_1$ inhomogeneities. In addition, $B_0$ homogeneity was sufficient to permit good water suppression in at least half of the wells in the plate. Roughly half of the 96 wells yielded usable spectra in this example. It is expected that this amount can be improved considerably through use of susceptibility-matched well caps (e.g., as described previously herein), or spherical wells (e.g., as described previously herein).

By showing that quality spectra of compounds in aqueous solution could be obtained using a standard-format well plate, this example illustrates that the goal of high-throughput NMR analysis of samples in susceptibility-matched well plates is possible. The success of the VAPOR water suppression sequence in attenuating the water signal in this example is a testament to the high $B_0$ field homogeneity that the susceptibility-matched well plate design makes possible. This homogeneity is also expected to result in improved spectral resolution and sensitivity relative to that achievable with conventional well plate designs and can facilitate the separation of signals from adjacent wells as well as the detection of small numbers of magnetic nanoparticles.

It is expected that further improvement in the number of wells yielding usable spectra can be obtained. For example, the assay plate may be moved during acquisition to bring individual wells (or groups of wells) into the field center of the magnet as they are being scanned, for example, using robotics, conveyor belts, or other automated devices known in the art in combination with computer-control. This is best appreciated by looking at FIG. 20A, where the geometric distortions are more pronounced along the Z (vertical) direction than along the X (horizontal) direction, at least near the center of the plate. According to one exemplary embodiment, the plate(s) may be moved along the axis of the magnet bore (Z-axis), for example, in a similar manner to what is done with a patient bed in a clinical MRI scanner. According to alternative embodiments, the plate(s) could additionally or alternatively be moved along the magnet's X- and/or Y-axes. Being able to move the plate along the X or Z axis would allow use of a smaller, more sensitive receive coil sized to only detect signal from a few wells at a time. Additionally or alternatively, software may be implemented to correct any residual non-uniformities in sensitivity and resolution between wells. For example, the reference deconvolution method may be implemented to mathematically correct the NMR signals from each well. See, K. R. Metz et al., Concepts Magn. Reson., 12(1):21-42 (2000) (incorporated herein by reference).

It is also expected that scanning throughput can be further improved. For example, multiple assay plates according to the present invention can be stacked (e.g., vertically upon one-another). This can take advantage of the good $B_1$ homogeneity and gradient linearity generally available along the scanner's Y-axis over the limited distance of the stack's thickness. Additionally or alternatively, scanning time may be reduced by measuring and storing optimum shim settings, RF pulse gains and water resonance frequencies for each well. This may greatly reduce scanning time by eliminating well-by-well optimization of these parameters for each sample in the assay plate, particularly in applications where samples do not vary much in magnetic susceptibility in corresponding wells in many plates (e.g. quality control assays). Additionally or alternatively, efficiency may be improved when using the PRESS sequence by interleaving excitations of multiple wells. For example, when scanning samples with long $T_1$ relaxation times, one well could be excited while simultaneously waiting for another well to relax, thereby acquiring signal-averaged spectra for multiple wells in an interleaved fashion.

The elimination of image distortions by the use of the susceptibility-matched plates and/or plugs and related techniques of the present invention provides substantial improvements over the prior art. For one, as demonstrated in the examples, above, the plates/caps according to the present invention can make it possible to simultaneously resolve localized NMR spectra for individual wells of a multi-well plate in high throughput NMR spectroscopy. As a result, the plates/plugs of the present invention are well suited for high-throughput NMR with moderate spectral resolution and sensitivity requirements, for instance, high-throughput NMR screening of drugs for impurities. The plates/caps of the present invention also facilitate observation of multiple chemical reactions simultaneously and under identical conditions. The plates/caps also facilitate comparison of the binding of different drugs to one or more enzymes using NMR spectroscopy. The plates/caps of the present invention also facilitate high throughput parallel chemical analysis using NMR, for example, of twenty samples or more.

In addition, the plates/caps of the present invention greatly improve detection levels in high-throughput MRI of magnetic nanoparticles. By reducing background field inhomogeneities, the plates/caps of the present invention can also facilitate the substitution of the gradient echo sequence (generally preferred for detecting magnetic nanoparticles) for the less sensitive spin echo sequence (as employed in the Högemann D. et al. reference, mentioned below), which is less prone to artifacts due to macroscopic inhomogeneities in the magnetic field. Likewise, the inventive plates/caps facilitate use of longer echo times in either spin echo or gradient echo MRI for improved sensitivity.

Hogemann D. et al., *High Throughput Magnetic Resonance Imaging for Evaluating Targeted Nanoparticle Probes*, Bioconjugate Chem., 13:116-121, 2002 (the entire content of which is incorporated herein by reference) discloses methods of using MRI to count magnetic nanoparticles in conventional (X unmatched) multi-well plates. Specifically, transferrin- and peptide-conjugated nanoparticles were used to detect the presence of specific receptors on cells. Performing the disclosed magnetoimmunoassay with the susceptibility-matched plates and/or caps of the present invention would provide surprising improvements in the detection limit for the magnetic nanoparticles by eliminating background signal losses due to susceptibility differences not caused by the magnetic particles.

Perez J. M. et al., *Nature Biotech.*, 20:816-820, 2002 (incorporated herein by reference) demonstrates many other applications for counting functionalized magnetic nanoparticles using MRI, including the selective detection of specific oligonucleotide sequences. Grimm J. et al., *Cancer Res.*, 64: 639-643, 2004, and Zhao et al., *Angew. Chem. Int. Ed.*, 42:1375-1378, 2003 (both of which are incorporated herein by reference) disclose the measurement of telomerase and other enzymatic activity by counting magnetic nanoparticles. Tsourkas A. et al., *Angew. Chem. Int. Ed.*, 43: 2395-2399, 2004 (incorporated herein by reference) discloses the detection of enantiomeric impurities in drug synthesis using similar techniques. Using the plates and/or caps of the invention provides unexpected improvements in such techniques.

The plates/caps of the present invention can also be used in clinical chemistry, for example, in high throughput screening of blood serum for different cholesterols. U.S. Patent Application Publication No. 2005/0222504, incorporated herein by reference, discloses techniques for lipo-profiling that could be practiced in high-throughput using the plates/caps of the present invention.

All of the above-described methods, and others apparent to a person of ordinary skill in the art, can be improved by using the plates of the present invention, e.g., by providing improved detection levels or by facilitating better resolution of NMR spectra, and by increasing throughput.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

The invention claimed is:

1. A method of performing high throughput magnetic resonance analysis of one or more samples, the method comprising:
   selecting a first sample having a first bulk magnetic susceptibility;
   selecting an assay plate constructed from a material having a second bulk magnetic susceptibility, the assay plate including a plurality of wells;
   introducing the first sample into at least one of the plurality of wells;
   inserting a cap into at least one or more of the plurality of the wells, wherein each cap is constructed from a material having a third bulk magnetic susceptibility wherein the cap includes one or more vent holes configured to permit air and/or the sample to be evacuated from the at least one of the plurality of wells; and
   performing magnetic resonance analysis on the plurality of wells of the assay plate, wherein performing magnetic resonance analysis individually on the wells of the assay plate comprises using the PRESS sequence to acquire NMR spectra from one well at a time.

2. The method of claim 1, wherein the step of selecting the assay plate comprises selecting the assay plate from a plurality of assay plates constructed from materials having different magnetic susceptibilities.

3. The method of claim 1, wherein magnetic resonance analysis is performed on another well of the assay plate without removing the first sample from any of the wells.

4. The method of claim 1, wherein the step of performing magnetic resonance analysis occurs in a horizontal bore MRI scanner.

5. The method of claim 1, wherein the step of performing magnetic resonance analysis comprises using MRI imaging to detect particles located in a plurality of the wells.

6. The method of claim 5, wherein the particles are magnetic nanoparticles.

7. The method of claim 6, wherein each of the magnetic nanoparticles is associated with a biological material.

8. The method of claim 7, wherein the biological material is selected from the group consisting of lipids, proteins, peptides, oligonucleotides, polysaccharides, tissue, cells, and cell fragments.

9. The method of claim 1, further comprising the steps of:
   introducing a second sample into at least one of the wells, the second sample having a bulk magnetic susceptibility within about 1% or less of the second bulk magnetic susceptibility; and
   performing magnetic resonance analysis on the at least one well containing the second sample.

10. The method of claim 1, wherein the assay plate and each cap are constructed from the same material.

11. The method of claim 1, wherein the assay plate is constructed from one of the polymers selected from the group consisting of polyetherimide, polyphenylene, sulphide, polyetheretherketone, acetal copolymer, glass-filled PEEK, and polyimide.

12. The method of claim 11, wherein the one or more samples include a solvent selected from the group consisting of water, heavy water, heavy dimethylsulfoxide, methylethylketone, carbon disulfide, methanol, diethyl ether, ethanol, trichloroethylene, glycerol, chloroform, and heavy chloroform.

13. The method of claim 1, further comprising the steps of:
   selecting a second assay plate constructed from a material having a bulk magnetic susceptibility within about 1% or less of the first and second bulk magnetic susceptibilities; and
   stacking the second assay plate on top of the assay plate.

14. The method of claim 1, further comprising the step of moving the assay plate within a horizontal bore of a MRI scanner to center individual wells or groups of wells with respect to a $B_0$ magnetic field.

15. The method of claim 1, further comprising the step of scanning multiple wells of the assay plate in an interleaved order.

16. The method of claim 1, further comprising the step of pre-mapping variations in $B_0$ and $B_1$, for a plurality of the wells.

17. The method of claim 1, further comprising the step of compensating for residual field inhomogeneities using software correction.

18. The method of claim 1, further comprising the steps of:
   determining the first bulk magnetic susceptibility of the first sample;
   determining the bulk magnetic susceptibility of an inventory of assay plates; and
   selecting an assay plate from the inventory, the selected assay plate having a second bulk magnetic susceptibility within about 1% or less of the first bulk magnetic susceptibility.

19. The method of claim 1, wherein the first sample is located in a solvent selected from the group consisting of water, heavy water, heavy dimethylsulfoxide, methylethylketone, methanol, diethyl ether, ethanol, trichloroethylene, glycerol, carbon disulfide, chloroform, and heavy chloroform; and the plate is constructed from one of the polymers selected from the group consisting of polyetherimide, polyphenylene sulphide, polyetheretherketone, acetal copolymer, glass-filled PEEK, and polyimide.

20. The method of claim 1, wherein the first sample comprises a neat liquid.

21. The method of claim 1, wherein the cap reduces the inhomogeneity in a magnetic field that surrounds the assay plate during magnetic resonance analysis.

22. The method of claim 1, wherein the cap substantially reduces the effects of mis-matched first and second bulk magnetic susceptibilities between the sample and the assay plate.

23. The method of claim 1, wherein the cap substantially reducing the effects caused by an air-sample interface, an assay plate-sample interface, and/or an assay plate-air interface.

24. The method of claim 1, wherein the cap comprises at least one of a plastic, a sponge, and a porous ceramic.

25. The method of claim 1, wherein the cap comprises a concave lower surface configured to funnel air bubbles from each of the plurality of wells of the assay plate.

26. The method of claim 1, wherein the assay plate and the cap are formed as an integral unit.

27. The method of claim 1, wherein each of the plurality of wells defines a substantially hemispherical depression located in a bottom surface of each of the plurality of wells, wherein each cap defines a substantially hemispherical-shaped bottom surface that comports with the substantially hemispherical depression of each of the plurality of wells when the cap is disposed within the well.

* * * * *